United States Patent
Riabov et al.

(10) Patent No.: US 9,785,755 B2
(45) Date of Patent: Oct. 10, 2017

(54) PREDICTIVE HYPOTHESIS EXPLORATION USING PLANNING

(71) Applicant: International Business Machines Corporation, Armonk, NY (US)

(72) Inventors: Anton V. Riabov, Ann Arbor, MI (US); Shirin Sohrabi Araghi, White Plains, NY (US); Octavian Udrea, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 639 days.

(21) Appl. No.: 14/283,867

(22) Filed: May 21, 2014

(65) Prior Publication Data

US 2015/0339580 A1    Nov. 26, 2015

(51) Int. Cl.
*G06F 21/00*    (2013.01)
*G06F 11/00*    (2006.01)
*G06Q 10/06*    (2012.01)

(52) U.S. Cl.
CPC ............ *G06F 21/00* (2013.01); *G06F 11/00* (2013.01); *G06Q 10/06* (2013.01)

(58) Field of Classification Search
None
See application file for complete search history.

(56) References Cited

U.S. PATENT DOCUMENTS

| | | |
|---|---|---|
| 5,122,801 A | 6/1992 | Hughes |
| 5,508,928 A | 4/1996 | Tran |
| 6,263,358 B1 * | 7/2001 | Lee .................... G06F 9/4881 718/100 |
| 6,438,741 B1 * | 8/2002 | Al-omari .......... G06F 17/30463 707/694 |
| 7,139,686 B1 | 11/2006 | Critz et al. |

(Continued)

FOREIGN PATENT DOCUMENTS

EP    443212    8/1991

OTHER PUBLICATIONS

Sohrabi, S., Udrea, O., Ranganathan, A. Composition of Flow-Based Applications with HTN Planning. International Scheduling and Planning Applications workshop, 2012, 1-7. Retrieved from http://researcher.ibm.com/researcher/view_pubs.php?person=us-ssohrab&t=1.

(Continued)

*Primary Examiner* — Paulinho E Smith
(74) *Attorney, Agent, or Firm* — Cahn & Samuels, LLP

(57) ABSTRACT

In at least one embodiment, a method and a system include receiving a trace into a hypotheses generator from a source a trace, translating the trace and a state transition model into a planning problem using the hypotheses generator, producing a set of plans for the trace using at least one planner, translating each plan into hypothesis using the hypotheses generator and/or the planner, and returning the hypotheses from the hypotheses generator. In a further embodiment, the trace includes at least one of a future observation and a past observation. In at least one embodiment, the system includes at least one planner that develops a set of plans, a hypothesis generator, a database, at least one analytic, and at least one sensor where the hypotheses generator and/or the at least one planner converts each plan into a respective hypothesis.

20 Claims, 24 Drawing Sheets

(56) References Cited

U.S. PATENT DOCUMENTS

| | | | |
|---|---|---|---|
| 7,370,022 B2 | 5/2008 | Gupta et al. | |
| 7,472,379 B2 | 12/2008 | Chessell et al. | |
| 7,617,224 B2 | 11/2009 | Moulckers et al. | |
| 7,962,430 B1* | 6/2011 | Heidenreich | G06N 5/04 706/45 |
| 8,799,189 B2 | 8/2014 | Schwoegler et al. | |
| 9,047,464 B2* | 6/2015 | Sambamurthy | G06F 21/55 |
| 2001/0049793 A1 | 12/2001 | Sugimoto | |
| 2003/0069869 A1* | 4/2003 | Gronau | G06Q 10/06 706/46 |
| 2003/0139902 A1* | 7/2003 | Geib | B01D 61/025 702/181 |
| 2003/0233569 A1* | 12/2003 | Geib | G06F 21/554 726/22 |
| 2006/0106477 A1 | 5/2006 | Miyashita | |
| 2007/0005523 A1 | 1/2007 | Maren | |
| 2007/0204020 A1* | 8/2007 | Anderson | G06Q 10/06 709/223 |
| 2007/0250331 A1* | 10/2007 | Liu | G06Q 10/00 709/200 |
| 2008/0016547 A1* | 1/2008 | Anderson | H04L 63/10 726/1 |
| 2008/0034439 A1* | 2/2008 | Chen | H04L 63/105 726/27 |
| 2008/0071716 A1* | 3/2008 | Anderson | G06N 5/04 706/45 |
| 2008/0196012 A1 | 8/2008 | Cohen et al. | |
| 2008/0243449 A1* | 10/2008 | Feblowitz | G06F 8/10 703/2 |
| 2008/0243450 A1* | 10/2008 | Feblowitz | G06F 8/10 703/2 |
| 2008/0243451 A1* | 10/2008 | Feblowitz | G06F 17/30516 703/2 |
| 2008/0244236 A1* | 10/2008 | Feblowitz | H04L 65/60 712/220 |
| 2008/0244540 A1* | 10/2008 | Feblowitz | G06F 8/10 717/143 |
| 2008/0250390 A1* | 10/2008 | Feblowitz | G06F 8/34 717/114 |
| 2008/0256549 A1* | 10/2008 | Liu | G06F 9/4881 718/106 |
| 2008/0288595 A1* | 11/2008 | Liu | G06Q 10/10 709/206 |
| 2008/0313595 A1* | 12/2008 | Boulineau | G06F 8/20 717/101 |
| 2009/0055344 A1 | 2/2009 | Dugan et al. | |
| 2009/0177910 A1* | 7/2009 | Liu | G06F 11/3664 714/2 |
| 2010/0011255 A1* | 1/2010 | de Kleer | G06Q 10/06 714/47.1 |
| 2010/0242120 A1* | 9/2010 | Anderson | G06Q 10/06 726/27 |
| 2011/0004863 A1* | 1/2011 | Feblowitz | G08G 1/04 717/105 |
| 2011/0060708 A1* | 3/2011 | Suzuki | G06N 99/005 706/12 |
| 2011/0087515 A1* | 4/2011 | Miller | G06Q 10/04 705/7.26 |
| 2011/0098056 A1 | 4/2011 | Rhoads et al. | |
| 2011/0107273 A1* | 5/2011 | Ranganathan | G06F 8/10 715/854 |
| 2011/0131557 A1 | 6/2011 | Bouillet et al. | |
| 2012/0030729 A1 | 2/2012 | Schwartz et al. | |
| 2012/0117015 A1 | 5/2012 | Sathish | |
| 2012/0233590 A1 | 9/2012 | Ranganathan et al. | |
| 2013/0024408 A1 | 1/2013 | Firminger et al. | |
| 2013/0080995 A1 | 3/2013 | Raza | |
| 2013/0232156 A1 | 9/2013 | Dunn et al. | |
| 2014/0040279 A1 | 2/2014 | Beygelzinner et al. | |
| 2014/0081896 A1* | 3/2014 | Ranganathan | G06N 5/02 706/48 |
| 2014/0282359 A1* | 9/2014 | Feblowitz | G06F 8/20 717/104 |
| 2014/0351184 A1* | 11/2014 | Bhowmick | G06Q 10/06 706/12 |
| 2014/0379615 A1* | 12/2014 | Brigham | G06N 99/005 706/11 |
| 2015/0339580 A1* | 11/2015 | Riabov | G06Q 10/06 706/11 |
| 2015/0339582 A1* | 11/2015 | Riabov | G06N 5/04 706/11 |
| 2016/0034305 A1* | 2/2016 | Shear | G06F 9/50 707/722 |
| 2016/0117602 A1* | 4/2016 | Hassanzadeh | G06N 5/022 706/11 |

OTHER PUBLICATIONS

Nguyen et al., Generating diverse plans to handle unknown and partially known user preferences, Jun. 18, 2012. Artificial Intelligence 190 (2012) 1-31.

Yoo., T., et al., "Stochastic Event Counter for Discrete-Event Systems Under Unreliable Observations", 2008 American Control Conference, INL/CON07-13239 Preprint, Jun. 2008, pp. 1-9.

Yen, J., "Finding the K Shortest Loopless Paths in a Network", Management Science, Jul. 1971, pp. 712-716, vol. 17, No. 11.

Ghallab et al., excerpts from "Automated Planning", 2004, pp. 1-30, Morgan Kaufmann Publishers, San Francisco, CA.

Office action in U.S. Appl. No. 14/283,945. Oct. 4, 2016, pp. 1-10.

"Google Maps", http://www.google.com/maps/@31.168934,-100.0768425,6z, retrieved Sep. 11, 2014, 1 page.

Aljazzar, Husain eet al., "K*: A Heuristic Search Algorithm for Finding the k Shortest Paths", Artificial Intelligence, Jul. 14, 2011, 39 pages.

Aslam, Javed A. et al.. "The Star Clustering Algorithm for Static and Dynamic Information Organization", journal of Graph Algorithms and Applications, vol. 8, No. 1, Revised Aug. 2004, pp. 95-129.

Botea, Adi et al., "Path Planning with Compressed All-Pairs Shortest Paths Data", Proceedings of the Twenty-Third International Conference on Automated Planning and Scheduling (ICAPS). http:www.aaai.org/ocs/index.php/ICAPS/ICAPS13/paper/viewFile/6002/6191, Rome, Italy, Jun. 10-14, 2013, 293-297.

Bryce, Daniel, "Landmark-Based Plan Distance Measures for Diverse Planning", Proceedings of the International Conference on Automated Planning and Scheduling (ICAPS), Portsmouth, New Hampshire, Jun. 21-26, 2014, pp. 56-64.

Chaudhuri, Surajit et al., "Robust and Efficient Fuzzy Match for Online Data Cleaning", SIGMOD 2003, San Diego, California, Jun. 9-12, 2003, 12 pages.

Coman, Alexandra et al., "Generating Diverse Plans Using Quantitative and Qualitative Plan Distance Metrics", Proceedings of the Twenty-Fifth AAAI Conference on Artificial Intelligence, San Francisco, California, Aug. 7-11, 2011, pp. 946-951.

Eppstein, David, "Finding the k Shortest Paths", Department of Information and Computer Science, http://www.ics.uci.edu/~eppstein/pubs/Epp-SJC-98.pdf, Mar. 31, 1997, 26 pages.

Filippone, Maurizio et al., "A survey of kernel and spectral methods for clustering", Pattern Recognition, vol. 41, Issue 1, http://lagis-vi.univ-lille1.fr/~lm/classpec/publi_classif/A_survey_of_kernel_and_spectral_methods_for_clustering_PR_2008.pdf, Jan. 2008, pp. 176-190.

Hassanzadeh, Oktie et al., "Creating probabilistic databases from duplicated data", VLDB Journal, vol. 18, No. 5, Oct. 2009, pp. 1141-1166.

Hassanzadeh, Oktie et al., "Framework for Evaluating Clustering Algorithms in Duplicate Detection", VLDB'09, Lyon, France, Aug. 24-28, 2009, 12 pages.

Hoffman, Walter et al., "A Method for the Solution of the Nth Best Path Problem", Journal of the ACM, vol. 6 (4), Oct. 1959, pp. 506-514.

Khouadjia, Mostepha et al., "Pareto-Based Multiobjective AI Planning", Proceedings of the Twenty-Third International Joint Conference on Artificial intelligence, Beijing, China, Aug. 3-9, 2013, pp. 2321-2327.

(56) References Cited

OTHER PUBLICATIONS

Myers, Karen L. et al., "Generating Qualitatively Different Plans through Metatheoretic Biases", In Proceedings of the 16th National Conference on Artificial Intelligence, (AAAI-99), Orlando, Florida, Jul. 18-22, 1999, 7 pages.
Nau, Dana S. et al., "Automated Planning—Theory and Practice", http://www.cs.umd.edu/~nau/planning/slides/, Elsevier, May 2004, 1 page.
Nguyen, Tuan A. et al., "Generating diverse plans to handle unknown and partially known user preferences", Artificial Intelligence (AIJ), vol. 190, Oct. 2012, pp. 1-31.
Riabov, Anton V. et al., "New Algorithms for the Top-K Planning Problem", Proceedings of the Scheduling and Planning Applications Workshop (SPARK) at the 24th International Conference on Automated Planning and Scheduling (ICAPS), Jun. 21-26, 2014, 7 pages.
Roberts, Mark et al., "Evaluating Diversity in Classical Planning", Proceedings of the 24th International Conference on Automated Planning and Scheduling (ICAPS), Portsmouth, New Hampshire, Jun. 21-26, 2014, 9 pages.
Sohrabi, Shirin et al., "Hypothesis Exploration for MAlware Detection using Planning", Proceedings of the Twentieth International Joint Conference on Artificial Intelligence, IJCAI-07, Hyderabad, India, Jan. 6-12, 2007, 7 pages.
Srivasta, Biplav et al., "Domain Independent Approaches for Finding Diverse Plans", Proceedings of the Twentieth International Joint Conference on Artificial Intelligence, IJCAI-07, Hyderabad, India, Jan. 6-12, 2007, 7 pages.
Sroka, Michal et al., "Exploring Metric Sensitivity of Planners for Generation of Pareto Frontiers", In Proc. of the 6th Starting AI Researchers' Symposium (STAIRS), Aug. 2012, pp. 306-317.
Xu, Rui et al., "Survey of Custering Algorithms", IEEE Transactions on Neural networks, vol. 16, No. 3, May 2005, pp. 645-678.
Youngren, Mark A. et al., "The Future Theater-Level Model: A Research Project Update", Proceedings of the 1994 Winter Simulation Conference; http://www.informs-sim.org/wsc94papers/1994_0121.pdf, Orlando, Florida, Dec. 11-14, 1994, pp. 829-834.
Zhu, Andy D. et al., "Shortest Path and Distance Queries on Road Networks: Towards Bridging Theory and Practice", arXiv:1304.2576v2 [cs.DS], http://arxiv.org/pdf/1304.2576v2.pdf, Apr. 24, 2013, 22 pages.
Office action mailed Oct. 31, 2016; U.S. Appl. No. 14/525,790; pp. 1-8.
Office action mailed Nov. 22, 2016; U.S. Appl. No. 14/745,899; pp. 1-8.
List of IBM Patents or Applications Treated as Related, pp. 1-2.
Aljazzar, H., et al., "K*: A Heuristic Search Algorithm for Finding the k Shortest Paths", Artificial Intelligence, pp. 2129-2154, vol. 175, No. 18.
Baier, J., et al., "Planning with Preferences", AI Magazine, 2008, pp. 25-36.
Baier, J., et al., "A heuristic search approach to planning with temporally extended preferences", Artificial Intelligence, 2009, pp. 593-618, vol. 173.
Bauer, A., et al., "Alarm Processing with Model-Based Diagnosis of Event Discrete Systems", Proceedings of the 22nd International Workshop on Principles of Diagnosis, 2011, pp. 52-59.
Benton, J., et al., "Temporal Planning with Preferences and Time-Dependent Continuous Costs", Proceedings of the 22nd International Conference on Automated Planning and Scheduling, 2012, pp. 1-9.
Blum, A., et al., "Fast planning through planning graph analysis", Artificial Intelligence, 1997, pp. 281-300, vol. 90.
Bonet, B., et al., "Planning as heuristic search", Artificial Intelligence, 2001, pp. 5-33, vol. 129, Nos. 1-2.
Botea, A., "Ultra-Fast Optimal Pathfinding without Runtime Search", Proceedings of the Seventh AAAI Conference on Artificial Intelligence and Interactive Digital Entertainment, 2011, pp. 1-6.
Botea, A., et al., "Path Planning with Compressed All-Pairs Shortest Paths Data", Proceedings of the Twenty-Third International Conference on Automated Planning and Scheduling, 2013, pp. 293-297.

Bouillet, E., et al., "MARIO: Middleware for Assembly and Deployment of Multi-platform Flow-Based Applications", Middleware, pp. 1-7, vol. 26.
Boutillier, C., et al., "CP-nets: A Tool for Representing and Reasoning with Conditional Ceteris Paribus Preference Statements", Journal of Artificial Intelligence Research, 2004, pp. 135-191, vol. 21, AI Access Foundation and Morgan Kaufmann Publishers.
Cordier, M., et al., "Event-Based Diagnosis for Evolutive Systems", Publication Interne N 819, May 1994, pp. 1-21.
Do, Minh, et al., "Planning with Goal Utility Dependencies", Proceedings of the 20th International Joint Conference on Artificial Intelligence, 2007, pp. 1872-1878.
Dvorak, D., et al., "Model-Based Monitoring of Dynamic Systems", Knowledge Representation, 1989, pp. 1238-1243.
Dvorak, D., et al., "Process Monitoring and Diagnosis: A Model-Based Approach", IEEE Expert, pp. 76-74, Jun. 1991, vol. 6, No. 3.
Edelkamp, S., et al., "Optimal Symbolic Planning with Action Costs and Preferences", Proceedings of the 21st International Joint Conference on Artificial Intelligence, 2009, pp. 1690-1695.
Edelkamp, S., et al., "Cost-Optimal Planning with Constraints and Preferences in Large State Spaces", Computer Science Department, University of Dortmund, Dortmund, Germany, 2006, pp. 1-8.
Eppstein, D., "Finding the k Shortest Paths", SIAM Journal on Computing, 1998, pp. 652-673, vol. 28, No. 2.
Gerevini, A., et al., "Deterministic planning in the fifth international planning competition: PDDL3 and experimental evaluation of the planners", Artificial Intelligence, 2009, pp. 619-668, vol. 173.
Ghallab, M., et al., "Automated Planning: theory and practice", 2004, pp. 27-41, Morgan Kaufmann Publishers.
Goebelbecker, M., et al., "Coming up With Good Excuses: What to do When no Plan Can be Found", Proceedings of the 20th International Conference on Automated Planning and Scheduling, 2010, pp. 81-88.
Goldman, R., et al., "A New Model of Plan Recognition", UAI, 1999, pp. 245-254.
Grastien, A., et al., "Diagnosis of Discrete-Event Systems Using Satisfiability Algorithms", Proceedings of the 22nd National Conference on Artificial Intelligence, 2007, pp. 305-310.
Grastein, A., et al., "Exhaustive Diagnosis of Discrete Event Systems through Exploration of the Hypothesis Space", Proceedings of the 22nd National Conference on Artificial Intelligence, 2011, pp. 1-8.
Haslum, P., et al., "Diagnosis as Planning: Two Case Studies", International Scheduling and Planning Applications Workshop (SPARK), 2011, pp. 27-44.
Hoffman, W., et al., "A Method for the Solution of the Nth Best Path Problem", Journal of the ACM, 1959, pp. 506-514, vol. 6, No. 4.
Hoffmann, J., et al., "The FF Planning System: Fast Plan Generation Through Heuristic Search", Journal of Artificial Intelligence Research, 2001, pp. 253-302, vol. 14.
Hsu, C., et al., "Constraint Partitioning for Solving Planning Problems with Trajectory Constraints and Goal Preferences", IJCAI, 2007, pp. 1924-1929.
Kambhampati, S., "Model-lite Planning for the Web Age Masses: The Challenges of Planning with Incomplete and Evolving Domain Models", Proceedings of the 22nd National Conference on Artificial Intelligence, 2007, pp. 1601-1604.
Keyder, E., et al., "Soft Goals Can Be Compiled Away", Journal of Artificial Intelligence Research, Dec. 2009, pp. 547-556, vol. 96.
Lin, N., et al., "Web Service Composition with User Preferences", S. Bechhofer et al. (Eds.): ESWC2008, LNCS 5021, 2008, pp. 629-643.
McDermott, D., et al., "PDDL—The Planning Domain Definition Language", Tech Report CVC TR-98-003/DCSTR-1165, Oct. 1998, pp. 1-27.
McIlraith, S., "Towards a Theory of Diagnosis, Testing and Repair", Proceedings of the 5th International Workshop on Principles of Diagnosis, 1994, pp. 185-192.
Mohanta, K., "Comprehensive Study on Computational Methods for K-Shortest Paths Problem", International Journal of Computer Applications, Feb. 2012, pp. 22-26, vol. 40, No. 14.

(56) References Cited

OTHER PUBLICATIONS

Myers, K., et al., "Generating Qualitatively Different Plans through Metatheoretic Biases", Proceedings of the 16th National Conference on Artificial Intelligence (AAAI), 1999, pp. 570-576.

Nguyen, T., et al., "Generating diverse plans to handle unknown and partially known user preferences", Artificial Intelligence, 2012, pp. 1-31, vol. 190.

Ramirez, M., et al., "Plan Recognition as Planning", Proceedings of the 21st International Joint Conference on Artificial Intelligence, 2009, pp. 1778-1783.

Riabov, A., et al., "New Algorithms for the Top-K Planning Problem", IBM T.J. Watson Research Center. Yorktown Heights, NY, pp. 1-7.

Richalet, J., "Industrial Applications of Model Based Predictive Control", Automatica, 1993, pp. 1251-1274, vol. 29, No. 5.

Richter, S., et al., "Landmarks Revisited", Proceedings of the Twenty-Third AAAI Conference on Artificial Intelligence, 2008, pp. 975-982.

Richter, S., et al., "The LAMA Planner: Guiding Cost-Based Anytime Planning with Landmarks", Journal of Artificial Intelligence Research, Oct. 2010, pp. 127-177, vol. 39.

Sampath, M., et al., "Diagnosability of Discrete-Event Systems", IEEE Transactions on Automatic Control, Sep. 1995, pp. 1555-1575, vol. 40, No. 9.

Sohrabi, S., et al., "Composition of Flow-Based Applications with HTN Planning", Problem Solving Using Classical Planners, AAAI Technical Report WS-12-12, pp. 58-64.

Sohrabi, S., et al., "Diagnosis as Planning Revisited", Proceedings of the Twelfth International Conference on the Principles of Knowledge Representation and Reasoning, 2010, pp. 26-36.

Sohrabi, S., et al., "HTN Planning with Preferences", Proceedings of the 21st International Joint Conference on Artificial Intelligence, 2009, pp. 1790-1797.

Sohrabi, S., et al., "Hypothesis Exploration for Malware Detection using Planning", Proceedings on the Twenty-Seventh AAAI Conference on Artificial Intelligence, 2013, pp. 883-889.

Sohrabi, S., et al., "Preferred Explanations: Theory and Generation via Planning", Proceedings of the Twenty-Fifth AAAI Conference on Artificial Intelligence, 2011, pp. 261-267.

Sohrabi, S., et al., "Web Service Composition via Generic Procedures and Customizing User Preferences", The Semantic Web—ISWC 2006, Lecture Notes in Computer Science, 2006, pp. 597-611, vol. 4723.

Srivastava, B., et al., "Domain independent Approaches for Finding Diverse Plans", Proceedings of the 20th International Joint Conference on Artificial Intelligence (IJCAI-07), 2007, pp. 2016-2022.

* cited by examiner

```
0. Find plan P for the original problem.
1. Add each action a of P as a separate action
   set S = {a} to future exploration list L.
2. For each set of actions S in L,
3.     For each action a ∈ S,
4.         Add negated predicate associated
           with a to the goal.
5.     Generate a plan P for the new problem
       where the goal disallows all actions in S.
6.     For each action a ∈ P,
7.         Add the set S ∪ {a} to L'
8. Move all action sets from L' to L.
9. Repeat from step 2.
```

FIG. 9

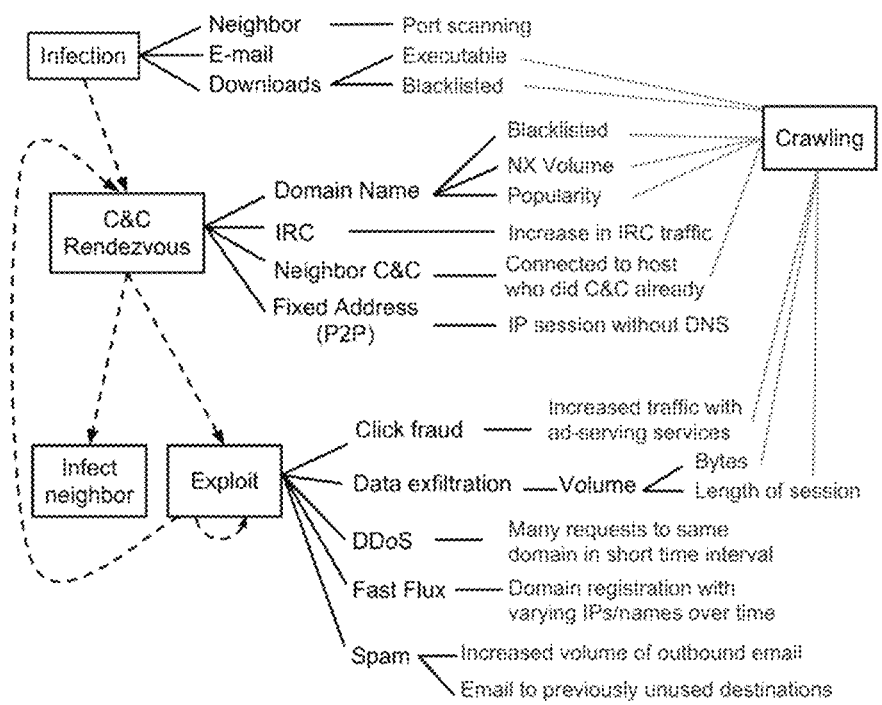

FIG. 10

```
default-class bad_state
LIFECYCLE=(start -> INFECTION |start -> SAFE)
SAFE=(reading_shared_disk(good_state OReadSharedDisk) -> SAFE
      |reading_shared_disk->INFECTION)
INFECTION=(download_code(ODownload) -> CC)
CC=(cc_darknet(ODarknet) -> INFECTED)
INFECTED=(portscan(OPortScan) -> INFECTED)
starting start
```

FIG. 11A

```
default-class bad_state
LIFECYCLE=(start(good_state) ->INFECTION|start->CRAWLING)
INFECTION= (infection_download_blacklisted(OBlacklisted)->CC|
           infection_download_exe(OExeDownloaded)->CC|
           infection_email(OEmailAttachment)->CC|
           infection_neighbor(OPortScanned)->CC)
CRAWLING =  crawl (good_state OContactedBlacklisted
           OHighNXVolume OHighAdTraffic OBlacklisted
           OExeDownloaded OHighSessionLen OHighVolume))
CC=(CC_DOMAIN(ODomainGenericAnomaly)->EXPLOIT|
    cc_p2p(OIPWoDNS)->EXPLOIT|
    cc_irc(OIncreaseInIRC)->EXPLOIT|
    cc_neighbor(OContactedNewNeighbor)->EXPLOIT)
CC_DOMAIN= cc_unpopular_domain(OContactedUnpopularDomain)|
           cc_blacklisted_domain(OContactedBlacklisted)|
           cc_domain_nxvolume(OHighNXVolume))
EXPLOIT=(bot_session_len(OHighSessionLen)->EXPLOIT|
         bot_clickfraud(OHighAdTraffic)->EXPLOIT|
         bot_fastflux(OContactFastFlux)->EXPLOIT|
         bot_spam_destination(ONewDest)->EXPLOIT|
         bot_volume_bytes(OHighVolume)->EXPLOIT|
         bot_ddos(OHighRequestsToDomain)->EXPLOIT|)
starting start
```

FIG. 11B

```
default-class bad_state
  LIFECYCLE=(start(-good_state-) -> INFECTION | start -> SAFE)
  SAFE=(reading_shared_disk(-good_state-,OReadSharedDisk,OFuture) -> SAFE
       | reading_shared_disk -> INFECTION)
  INFECTION=(download_code(ODownload,OFuture) -> CC)
  CC=(cc_darknet(ODarknet,OFuture) -> INFECTED)
  INFECTED=(portscan(OPortScan,OFuture) -> INFECTED)
  starting start
```

```
default-class bad_state
LIFECYCLE=(start (good_state)->INFECTION|start->CRAWLING)
INFECTION=(infection_download_blacklisted(OBlacklisted OFuture)->CC|
          infection_download_exe(OExeDownloaded OFuture)->CC|
          infection_email(OEmailAttachment)->CC|
          infection_neighbor(OPortScanned OFuture)->CC)
CRAWLING = (crawl (good_state OContactedBlacklisted
          OHighNXVolume OHighAdTraffic OBlacklisted
          OExeDownloaded OHighSessionLen OHighVolume OFuture))
CC=(CC_DOMAIN(ODomainGenericAnomaly)->EXPLOIT|
 cc_p2p(OIPWoDNS)->EXPLOIT|cc_irc(OIncreaseInIRC OFuture)->EXPLOIT|
 cc_neighbor(OContactedNewNeighbor OFuture)->EXPLOIT)
CC_DOMAIN=(cc_unpopular_domain(OContactedUnpopularDomain OFuture)|
 cc_blacklisted_domain(OContactedBlacklisted OFuture)|
 cc_domain_nxvolume(OHighNXVolume OFuture))
EXPLOIT=(bot_session_len(OHighSessionLen OFuture)->EXPLOIT|
 bot_clickfraud(OHighAdTraffic OFuture)->EXPLOIT|
 bot_fastflux(OContactFastFlux OFuture)->EXPLOIT|
 bot_spam_destination(ONewDest OFuture)->EXPLOIT|
 bot_volume_bytes(OHighVolume OFuture)->EXPLOIT|
 bot_ddos(OHighRequestsToDomain OFuture)->EXPLOIT|)
starting start
```

FIG. 12B

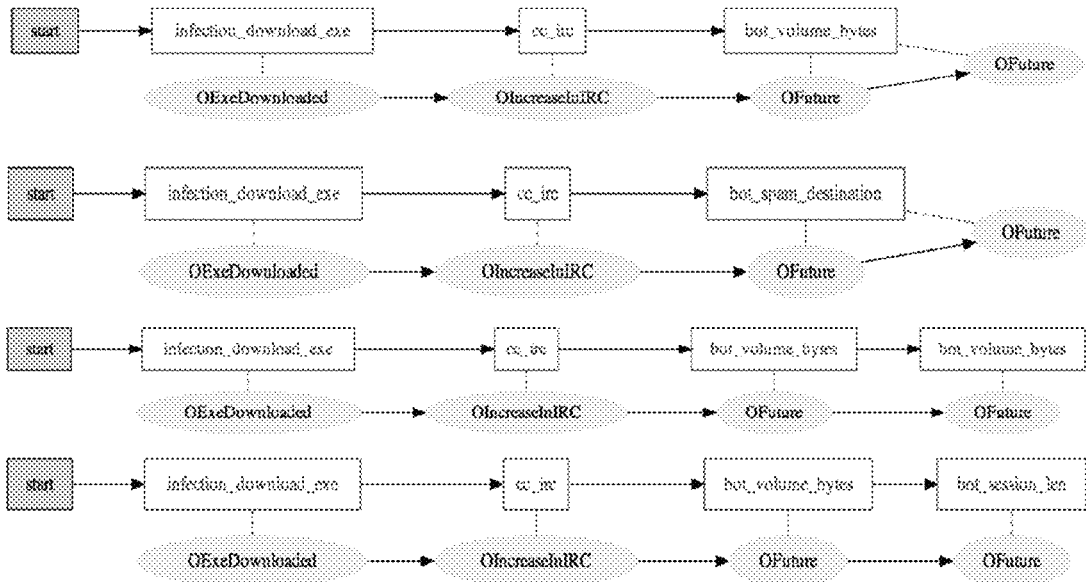

FIG. 12C

```
default-class bad_state
LIFECYCLE = (start <good_state>) -> INFECTION | start -> CRAWLING
INFECTION = (infection_download_exe <OExeDownloaded> -> CC |
             infection_email <OEmailAttachment> -> CC |
             infection_neighbor ::highest_imp <OPortScanned> -> CC |
             infection_blacklisted <OBlacklistedDomain> -> CC)

CRAWLING = (crawl <good_state::low_imp> OContactedBlacklisted
            OHighNXVolume OHighAdTraffic OBlacklisted
            OExeDownloaded OHighSessionLen OHighVolume>)

CC = (CC_DOMAIN <::highest_imp> ODomainGenericAnomaly) -> EXPLOIT |
     cc_irc (::low_imp> OIncreaseInIRC) -> EXPLOIT |
     cc_neighbor ::highest_imp <OContactedNewNeighbor> -> EXPLOIT |
     cc_p2p (OIPWODNS) -> EXPLOIT)
CC_DOMAIN = (cc_blacklisted_domain <OContactedBlacklisted> |
             cc_domain_nxvolume <OHighNXVolume> |
             cc_unpopular_domain <OContactedUnpopularDomain>)

EXPLOIT = (bot_fastflux <::highest_imp> OContactFastFlux) -> EXPLOIT |
          bot_ddos (::high_imp> OHighRequestsToDomain) -> EXPLOIT |
          bot_clickfraud <OHighAdTraffic> -> EXPLOIT |
          bot_session_len <OHighSessionLen> -> EXPLOIT |
          bot_spam_destination <ONewDest> -> EXPLOIT |
          bot_spam_outbound <OHighOutgoingVolume> -> EXPLOIT |
          bot_volume_bytes <OHighVolume> -> EXPLOIT)

starting start
```

FIG. 12E

PREDICTIVE HYPOTHESIS EXPLORATION USING PLANNING

STATEMENT REGARDING FEDERALLY SPONSORED RESEARCH OR DEVELOPMENT

This invention was made with Government support under Contract No.: H98230-11-C-0276 awarded by Department of Defense (DOD). The Government has certain rights in this invention.

SUMMARY OF THE INVENTION

The invention in at least one embodiment includes a method for operation of a system for predicting hypotheses, the method including: receiving a trace from a source of a trace, where a hypotheses generator receives the trace; translating the trace and a state transition model into a planning problem using the hypotheses generator; producing a set of plans for the trace using at least one planner; translating each plan into hypothesis using the hypotheses generator and/or the at least one planner; and returning the hypotheses from the hypotheses generator, and wherein the set of plans includes at least one top-quality plan and the hypotheses include at least one plausible hypothesis.

The invention in at least one embodiment includes a method for operation of a system for predicting hypotheses, the method including: receiving a trace including a request for at least one future observation or at least one past observation into a hypotheses generator in the system from a source of a trace; translating the trace and a state transition model into a planning problem using the hypotheses generator; producing a set of plans for the trace using at least one planner; translating each plan into a hypothesis using the hypotheses generator and/or the at least one planner where at least one hypothesis includes at least one of a future state and a past state; and returning the hypotheses from the hypotheses generator, and wherein the set of plans includes at least one top-quality plan and the hypotheses include at least one plausible hypothesis.

In a further embodiment to either of the prior embodiments, returning the hypotheses includes the score provided by the at least one planner for each plan based on the cost of the plan associated with the hypothesis and ordering the hypotheses based on the scores of the respective plans. In at least one embodiment, the scores for individual plans are based on the sum of the action costs for the actions present in that plan. Further to the prior embodiment, at least one of the following: action costs for less probable actions is higher than action costs for more probable actions, bad states have a higher action cost than good states, and malicious actions have a higher action cost than non-malicious actions. Further to any of the above embodiments, returning the hypotheses includes displaying each hypothesis by the hypotheses generator through a display including any observations present in the trace and the states with linkages between a plurality of the observations and the states. Further to any of the above embodiments, the method further includes at least one of requesting additional observations; and alerting an individual of any potential problem determined based on the generated hypotheses where the top hypotheses is indicative of a problem. Further to any of the above embodiments, producing top-plausible hypotheses includes finding at least one plan; eliminating at least one action from the found plan before finding another plan; and repeating the eliminating step k−1 times. Further to any of the above embodiments, producing top-quality plans includes finding at least one plan P; adding each action $\alpha$ of plan P as a separate action set $S=\{\alpha\}$ to a future exploration list L; for each set of actions S in list L, performing for each action $\alpha \in S$, adding negated predicate associated with $\alpha$ to the goal, generating a new plan P for the new problem where the goal disallows all actions in S, for each action $\alpha \in P$, adding the set $S \cup \{\alpha\}$ to list L', moving all action sets from list L' to list L, and repeating the previous three steps until a predetermined threshold is reached.

Further to any of the above embodiments, the method further includes returning future observations for at least one hypothesis returned by the hypotheses generator. Further to any of the above embodiments, the method further includes generating a new planning problem (and set of hypotheses) when a new trace or a new state transition model is received by the system.

The invention in at least one embodiment for each of the above method embodiments includes a computer program product for providing predictive hypotheses using planning, the computer program product including a computer readable storage medium having encoded thereon program instructions executable by a processor to cause the processor to perform the method steps of the prior embodiments irrespective of reference to particular components.

The invention in at least one embodiment includes a computer program product for predicting hypotheses, the computer program product comprising: a computer readable storage medium having encoded thereon: first program instructions executable by a processor to cause the processor to receive a trace; second program instructions executable by a processor to cause the processor to translate the trace and a state transition model into a planning problem; third program instructions executable by a processor to cause the processor to produce a set of plans for the trace; fourth program instructions executable by a processor to cause the processor to translate each plan into a hypothesis; fifth program instructions executable by a processor to cause the processor to return the hypotheses; and wherein the set of plans includes at least one of top-quality plans and the hypotheses includes at least one plausible hypothesis. In an alternative embodiment, the set of plans is top-k plans.

The invention in at least one embodiment includes a computer program product for predicting hypotheses, the computer program product comprising: a computer readable storage medium having encoded thereon: first program instructions executable by a processor to cause the processor to receive a trace including a request for at least one future observation or at least one past observation; second program instructions executable by a processor to cause the processor to translate the trace and a state transition model into a planning problem; third program instructions executable by a processor to cause the processor to produce a set of plans for the trace; fourth program instructions executable by a processor to cause the processor to translate each plan into a hypothesis where at least one hypothesis includes at least one of a future state and one past state; fifth program instructions executable by a processor to cause the processor to return the hypotheses; and wherein the set of plans includes at least one of top-quality plans and the hypotheses include at least one plausible hypothesis. In an alternative embodiment, the set of plans is top-k plans.

Further to any of the embodiments of the previous two paragraphs, the computer readable storage medium having further encoded thereon sixth program instructions executable by a processor to cause the processor to display each hypothesis through a display including any observations present in the trace and the states with linkages between a plurality of the observations and the states.

Further to any of the embodiments of the previous three paragraphs, the computer readable storage medium having further encoded thereon additional program instructions executable by a processor to cause the processor to return future observations for at least one hypothesis.

The invention in at least one embodiment includes a system including: at least one planner for the development of a set of plans; a hypothesis generator in communication with the at least one planner; a database in communication with the hypothesis generator and the at least one planner; at least one analytic in communication with the hypotheses generator and the database; and at least one sensor in communication with one of the at least one analytic, and wherein at least one of the hypotheses generator and the at least one planner converts each plan in the set of plans into a hypothesis. Further to the prior embodiment, the at least one analytic converts the data received from the at least one sensor into observations that are at least one of stored in the database and communicated with the hypotheses generator. Further to any of the prior embodiments in this paragraph, the hypotheses generator converts the observations along with a state transition model into a planning problem that is provided to the at least one planner. Further to any of the prior embodiments in this paragraph the hypotheses generator inserts at least one past observation or at least one future observation into the planning problem. Further to any of the prior embodiments in this paragraph the at least one planner determines a plan cost for each plan based on predetermined costs for the actions present in the plan. Further to the previous embodiment, the hypotheses generator displays each of the resulting hypotheses with a respective score based on the plan cost.

In at least one embodiment, the invention includes a method including: receiving with at least one processor identification of at least one entity in the model; receiving with the at least one processor identification of a plurality of states of the at least one entity; receiving with the at least one processor identification of a set of observations; receiving with the at least one processor a plurality of possible transitions between states; receiving with the at least one processor associations between observations and states; receiving with the at least one processor relative plausibility of each state; providing with the at least one processor a graphical representation of the received information as a model of a system; receiving with the at least one processor at least one debugging change regarding the received information; and testing with the at least one processor the model of the system. In a further embodiment, the method further includes receiving with the at least one processor designations of at least one state as at least one starting state. In a further embodiment to either of the prior two embodiments, the states includes at least one hyperstate.

BRIEF DESCRIPTION OF DRAWINGS

The present invention is described with reference to the accompanying drawings. In the drawings, like reference numbers indicate identical or functionally similar elements.

FIG. 9 illustrates a replanning process of at least one embodiment according to the invention.

FIG. 10 illustrates an example of a lifecycle for one of the applications.

FIGS. 11A and 11B illustrate examples of defined states, transitions, observations and state types. FIGS. 11C and 11D illustrate hypotheses generated based on FIGS. 11A and 11B.

FIGS. 12A and 12B illustrate examples of defined states, transitions, observations and state types for future state hypotheses. FIG. 12C illustrates hypotheses generated based on FIG. 12B. FIG. 12E illustrates another example encoding of future states hypotheses.

DETAILED DESCRIPTION

Figure 1:
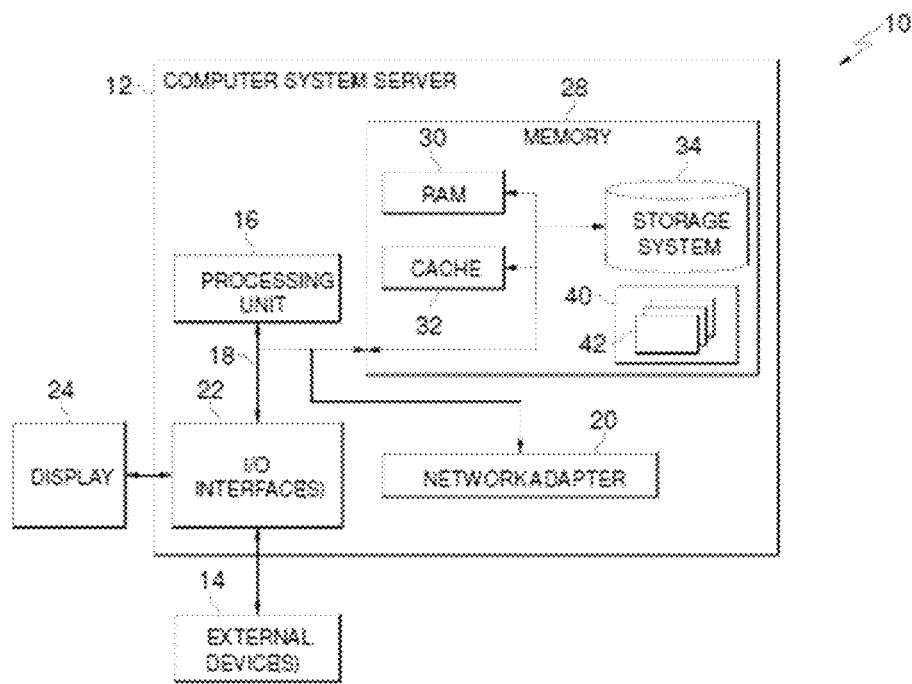
FIG. 1 illustrates a cloud computing node according to an embodiment of the present invention.

Exemplary, non-limiting, embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
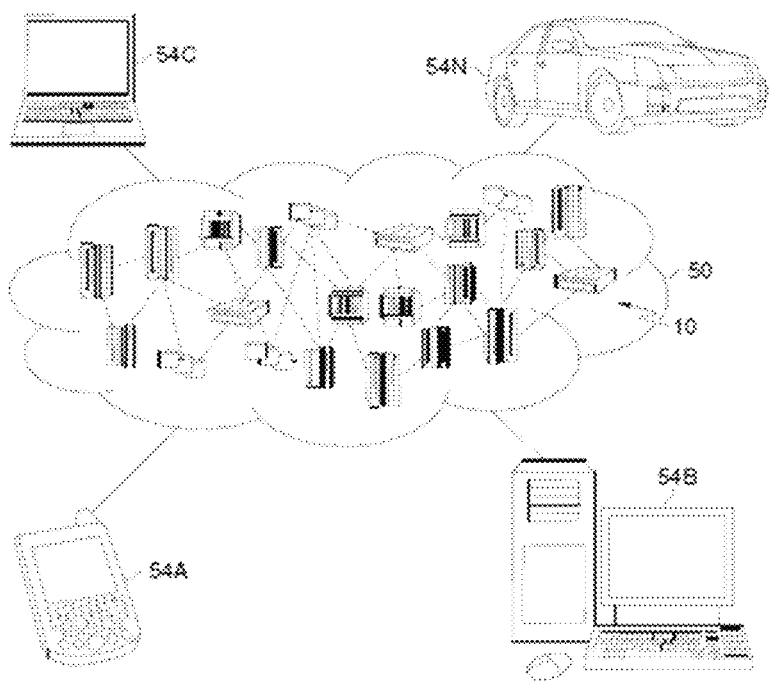
FIG. 2 illustrates a cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
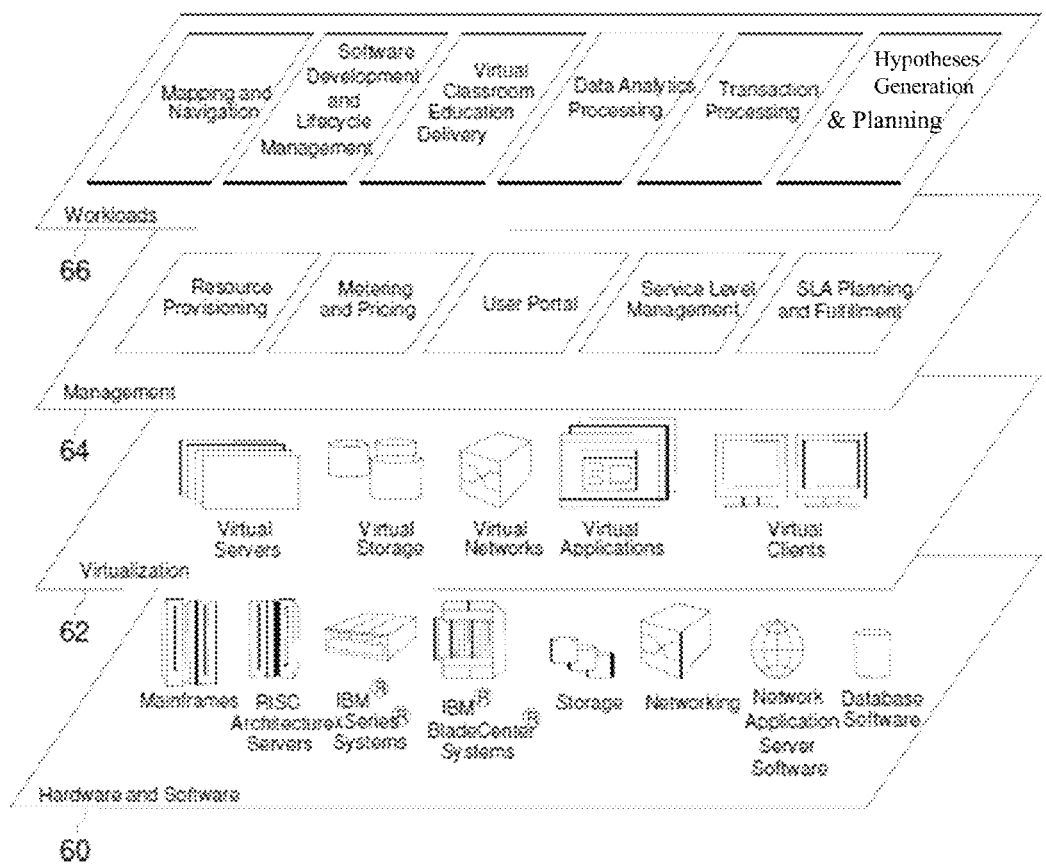
FIG. 3 illustrates abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided: Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 62 provides an abstraction layer from which the following examples of virtual entities may be provided: virtual servers; virtual storage; virtual networks, including virtual private networks; virtual applications and operating systems; and virtual clients.

In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide prearrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; transaction processing; hypotheses generation; and planning.

The invention in at least one embodiment relates to the field of automated Artificial Intelligence (AI) planning and its use for hypotheses generation, and an overview of such automated planning will be provided. Further information regarding automated planning can be found, for example, in Ghallab et al., "Automated Planning—Theory and Practice" (2004).

A planning problem consists of the following main elements: a finite set of facts, the initial state (a set of facts that are true initially), a finite set of action operators, and the goal condition. An action operator (or planning action) maps a state into another state. In classical planning, the objective is to find a sequence of action operators which when applied to the initial state, will produce a state that satisfies the goal condition. This sequence of action operators is called a plan. In at least one embodiment of the invention, high-quality plans are found instead of just any plan, the set of action operators may have numerical costs associated with them, and no goal may be provided.

In classical setting, quality often means the shortest plan so that the quality of a plan is measured based on the number of actions in the plan. Therefore, the best quality plan, or the optimal plan, often means a plan with the smallest number of action operators. According to at least one embodiment, the quality of the plan is measured based on the sum of the cost of the actions in the plan. Hence, a plan with minimum action costs is the highest-quality plan. According to at least one embodiment, the planner finds top-quality or near top-quality plans. That is it finds plans with minimum cost or close to minimum cost. In the case of top-K quality plans, the planner finds k top-quality plans with respect to the plan costs.

Several application scenarios require the construction of hypotheses presenting alternative explanation of a sequence of possibly unreliable observations. For example, the evolution of the state of the patient over time in an Intensive Care Unit (ICU) of a hospital can be inferred from a variety of measurements captured by patient monitoring devices, the results of computations done based on these measurements, as well as other measurements and computations provided by doctors and nurses. The hypotheses, represented as a sequence of changes in patient state (e.g., low risk, high risk, infection), aim to present an explanation for these observations (e.g., heart rate variability and SIRS), while providing deeper insight into the actual underlying causes for these observations, helping to make decisions about further testing, treatment or other actions. The plausibility of a hypothesis is measured by determining whether the states included in the hypotheses plausibly explain the corresponding observations, in the order they are received, and that the sequence of state transitions is also plausible.

A new approach for developing hypotheses, which in at least one embodiment are predictive hypotheses, that in at least one embodiment can not only generate hypotheses explaining past observations, but can also extend these hypotheses past the latest observation, generating possible future scenarios. Similarly, the method in at least one embodiment can extend the hypotheses to include the most plausible state transitions that could have happened before the first observation.

At a high level, the hypothesis generation approach in at least one embodiment uses a planner to generate a set of hypotheses, which explain observations by underlying state transitions that happen according to a model of a system. Examples of the set of hypotheses include hypotheses for top quality plans, most (or top) plausible hypotheses, and hypotheses from top-k plans. The model of the system would be translated into a planning problem and encoded in a planning domain description language, for example, PDDL (PDDL—Planning Domain Definition Language) or similar, with actions corresponding to explaining observations based on system state and actions that change system state, possibly with additional actions that connect the two types of actions, and possibly some actions that both explain observations and change system state. The planning problem would include the observed transition sequence, with the goal of explaining all observations in the observed sequence by observations generated by the simulated system. This may require additional actions in the planning domain that, in essence, establish the connection between the simulated states and observed observations, and therefore to measure the degree of plausibility of the hypothesis. If these conditions are met, the planner that produces top-k plans will, in effect, produce top-k hypotheses. In classical planning, a planning problem includes a definition of actions, which is sometimes referred to as a planning domain.

Figure 4:
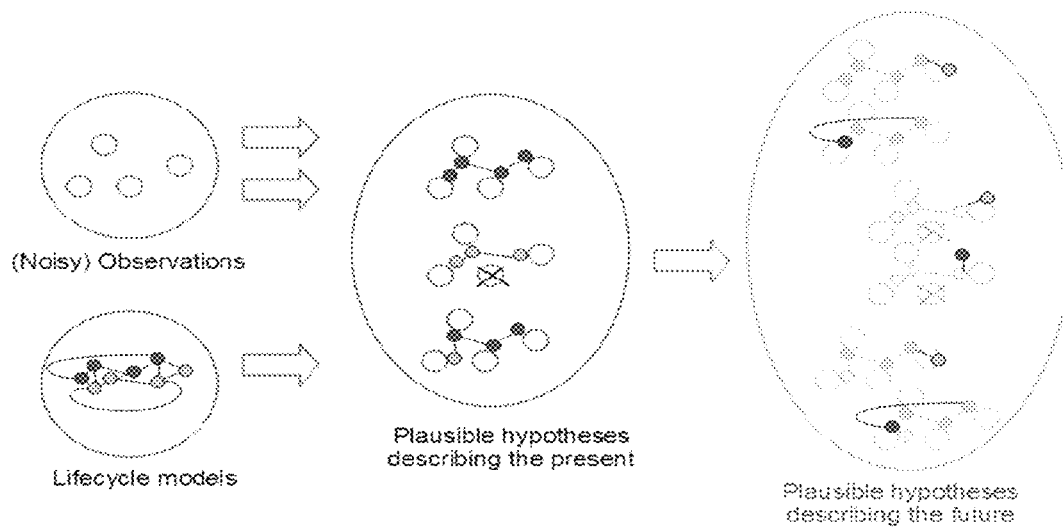
FIG. 4 illustrates an conceptual illustration of generating from a set of observations and a lifecycle state transition model of a system to hypotheses explain the present and to projections of possible present states into the future, generating new state transitions.

The diagram illustrated in FIG. 4 is a conceptual illustration of generating from a set of observations and a lifecycle state transition model of the system, with good (lighter colored small circles) and bad (darker colored small circles) states, to hypotheses explaining the present (possibly, discarding some observations), and to projections of possible present states into the future, generating new transitions. In practice, the states and the observations do not have two dimensional (2-D) coordinates, and plausibility is not determined using Euclidean distances, but the illustration is a helpful analogy for illustration purposes.

To show how this high-level idea can be realized in practice, an assumption that the model of the system is provided in at least one embodiment in a simpler, less expressive language than PDDL that will be called LTS++, but the approach can be generalized to more complex PDDL models of state transitions. LTS++ is a language derived from LTS (Labeled Transition System) for defining models for hypothesis generation, and associating observation types with states of the lifecycle. The examples in this disclosure will use LTS++ for illustrative purposes although other languages may be used instead.

Figure 5:
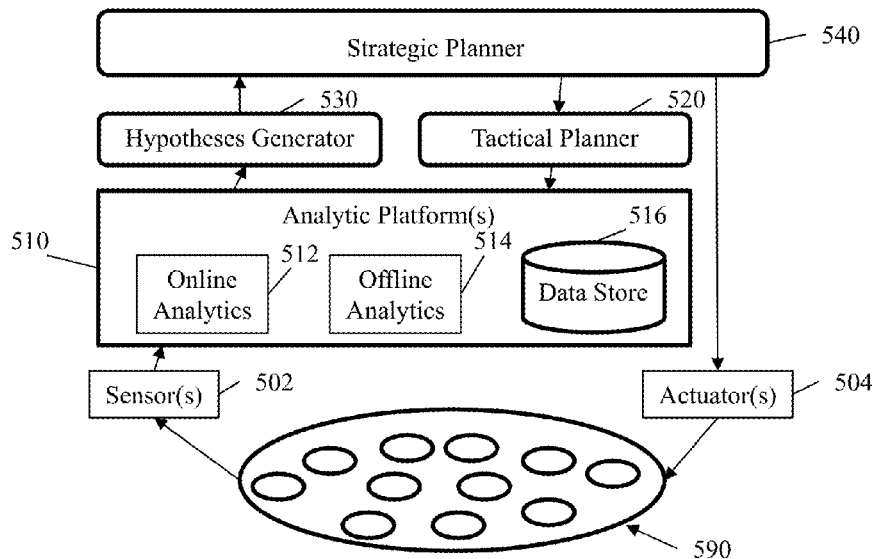
FIG. 5 illustrates a system of at least one embodiment according to the invention.

FIG. 5 illustrates an example system according to at least one embodiment of the invention. The automated exploration of hypotheses in at least one embodiment focuses on the hypothesis generation, which is part of a larger automated data analysis system that includes sensors 502, actuators 504, multiple analytic platforms 510 and a tactical planner 520. The tactical planner 520 in at least one embodiment may be viewed as a component responsible for execution of certain strategic actions and it can be implemented using, for example, a classical planner to compose analytics. All components of the architecture, with the exception of application-specific analytics 510, sensors 502, and actuators 504, are designed to be reused without modification in a variety of application domains such as malware detection and healthcare. In at least one embodiment, the analytic platform(s) 510, the tactical planner 520, the hypotheses generator 530, and the strategic planner 540 are software modules providing particular instructions for controlling the operation of at least one processor. In at least one embodiment, the tactical planner 520 and the strategic planner 540 are together one planner.

The illustrated system receives input from sensors 502 and analytics 512, 514 translate sensor data to observations. The hypothesis generator 530 interprets the observations received from analytics 510 and generates hypotheses about the state of entities 590 in the world (or the system that has been modeled). Depending on the application domain, the entities may correspond to patients in a hospital, computers connected to a corporate network, or other kinds of objects of interest. The strategic planner 540 evaluates these hypotheses and initiates preventive or testing actions in response. Some of the testing actions can be implemented as additional processing of data setting new goals for the tactical planner 520, which composes and deploys analytics across multiple analytic platforms 510. A Hadoop cluster, for example, can be used as an analytic platform for offline analysis by the offline analytics 514 of historical data accumulated in one or more data stores 516. Alternatively, a stream computing cluster can be used for fast online analysis by the online analytics 512 of new data received from the sensors 502. Based on this disclosure, one of ordinary skill in the art should appreciate the online analytics or the offline analytics may be omitted.

Preventive actions, as well as some of the testing actions, are dispatched to actuators 504. There is no expectation that every actuation request will succeed or always happen instantaneously. Actuation in a hospital setting can involve dispatching alerts to doctors or lab test recommendations.

In at least one embodiment, there is a system for generating hypotheses and developing state transition models, which system was used in the below described applications and experiments. In this particular embodiment, a language called LTS++ that can be used to represent the state transition system is used. Below is described a process that the user or the domain expert might undergo in order to define an LTS++ model. With examples provided using the system, which in at least one embodiment includes an integrated development environment (IDE) and the LTS++ syntax. In a further embodiment, the system includes a reusable and/or modular web-based system.

Figure 6:
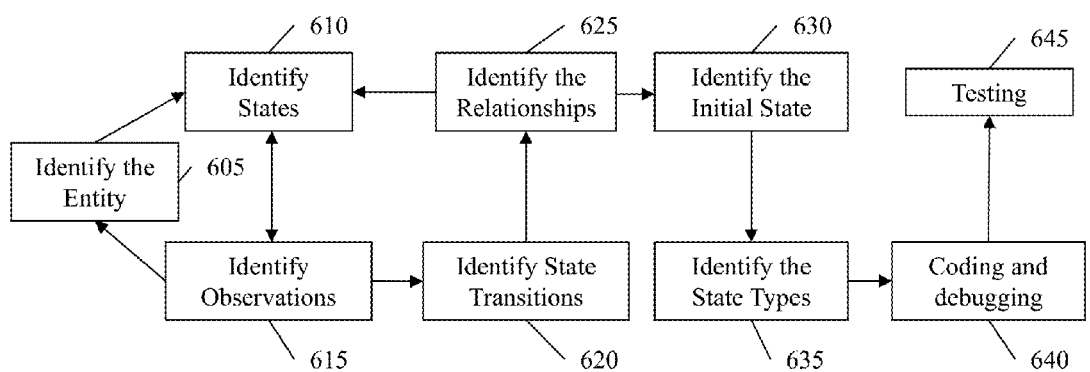
FIG. 6 illustrates a method of at least one embodiment according to the invention.

FIG. 6 illustrates a creation method for an LTS++ model. The arrows are intended to indicate the most typical transitions between steps: transitions that are not shown are not prohibited. This process and the arrows between the processes help provide guidance in developing an LTS++ model. In at least one embodiment, as part of the steps, the system translates the identifications into the LTS++ syntax. In at least one embodiment, identification of at least one entity in the model is made by, for example, the user, 605. This may depend on the objective of the hypothesis generator, the available data, and the available actions. For example, in the malware detection problem, the entity is the host, while in the intensive care delivery problem the entity is the patient.

Identification of the states of the entity from, for example, a domain expert is provided, 610. As discussed below in the application section, the states of a patient, for example, could be DCI (Delayed Cerebral Ischemia), infection, and high risk. Since the state transition model is manually specified and contains a fixed set of observation types, while potentially trying to model an open world with an unlimited number of possible states and observations, the model can be incomplete at any time, and may not support precise explanations for all observation sequences. To address this, and provide feedback to model designers about states that may need to be added, a hierarchical decomposition of states is used in at least one embodiment.

In at least one further embodiment, the method allows designating a subset of the state transition system as a hyperstate. In this case, if a transition through one or several states of the hyperstate is required, but no specific observation is associated with the transition, the hyperstate itself is included as part of the hypothesis, indicating that the model may have a missing state within the hyperstate, and that state in turn may need a new observation type associated with it. In the malware detection problem, the infection, exploit, cc_rendevouz are examples of hyperstates.

Figure 13A:
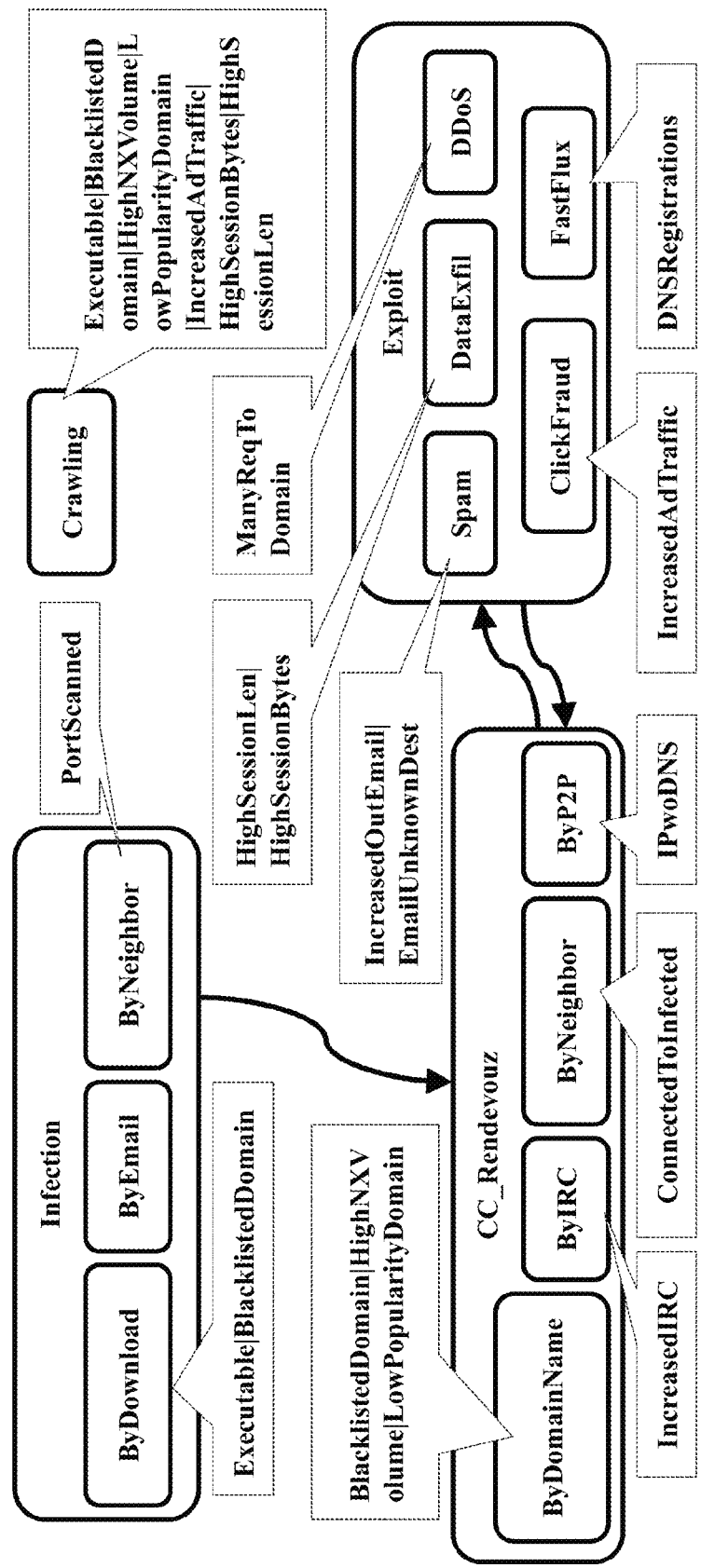
FIG. 13A illustrates another example of the lifecycle (or state transition system) illustrated in FIG. 10 where observations are linked to states.
Figure 15A:
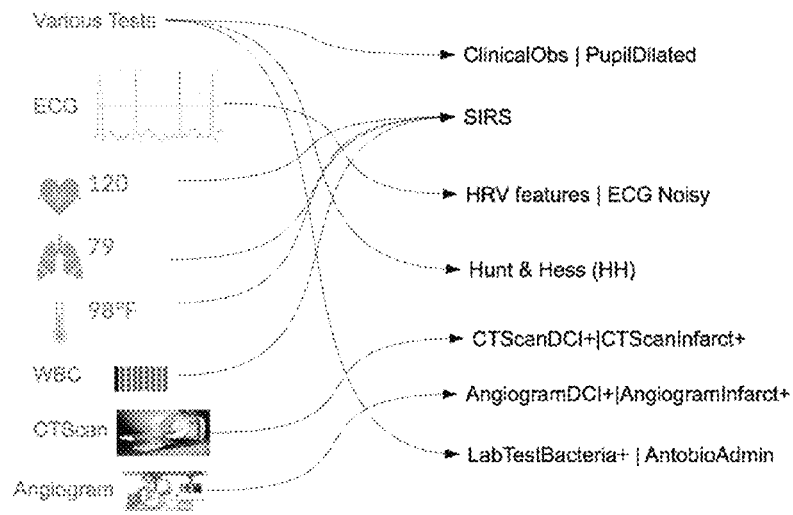
FIGS. 15A and 15B illustrate aspects of another application with FIG. 15A illustrating the observation space and FIG. 15B illustrating sample state transition system for the application.
Figure 15B:
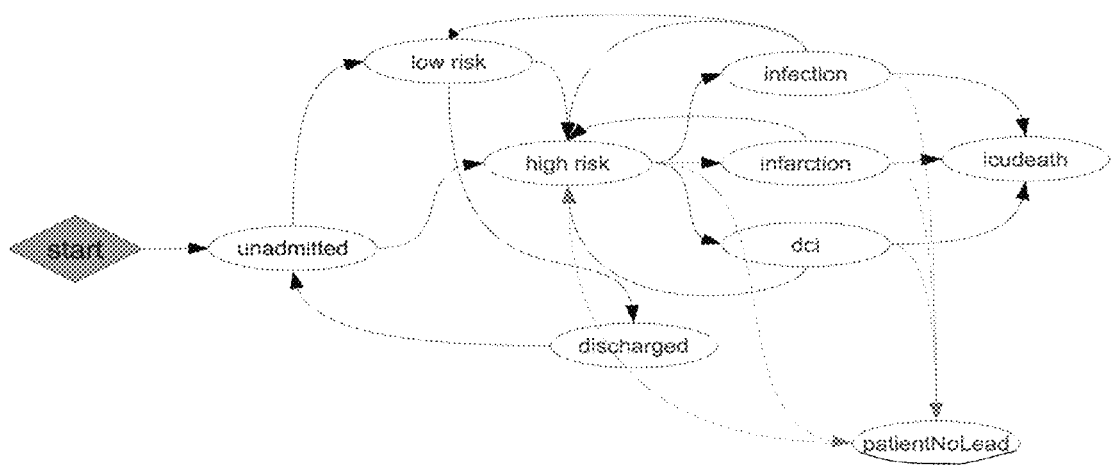
Figure 15C:
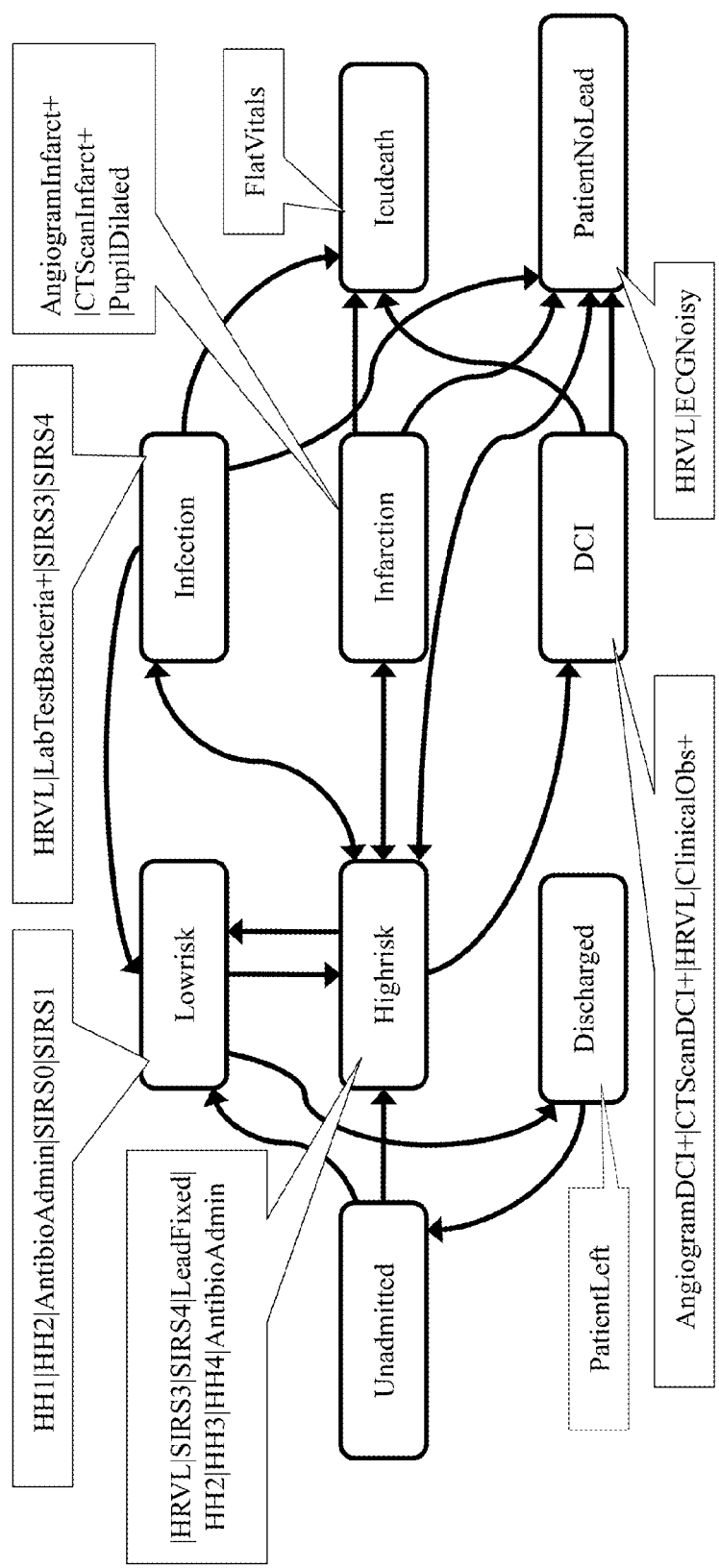
FIG. 15C illustrates another view of is the lifecycle (or state transition system) illustrated in FIG. 15B where observations are linked to states.

Identification of a set of observations for the particular problem is provided by, for example, the domain expert, 615. The available data, the entity, and the identified states may help define and restrict the space of observations. The possible transitions between states are provided by, for example, the domain expert, 620. In at least one embodiment, the possible transitions include all known transitions. This may be a tedious task for the domain expert to compile, depending on the number of states. However, one can use hyperstates to help manage these transitions. Any transition of the hyperstates is carried out to its substates. The associations between observations and states are provided by, for example, the user, 625. These associations are illustrated in FIGS. 13A and 15C using the callouts.

In an optional embodiment, the designations of a state as the starting state are provided, 630. The domain expert can also create a separate starting state that indicates a one of notation by transitioning to multiple states where the system receives the starting state. For example, in the malware detection problem, the starting state "start" indicates a "one of" notation as it transitions to both "CC" and "INFECTION".

An indication about each state type that indicates that some states are more plausible than the others are provided by, for example, the user, 635. In a further embodiment, the indication is a score value (or plan cost) for each state type. In a further embodiment, state types are related to the "good" vs. "bad" behaviors and they influence the ranking between hypotheses. For example, the hypothesis that the host is crawling is more plausible than there being an infection for the same trace which can be explained by both hypotheses.

Figure 8:
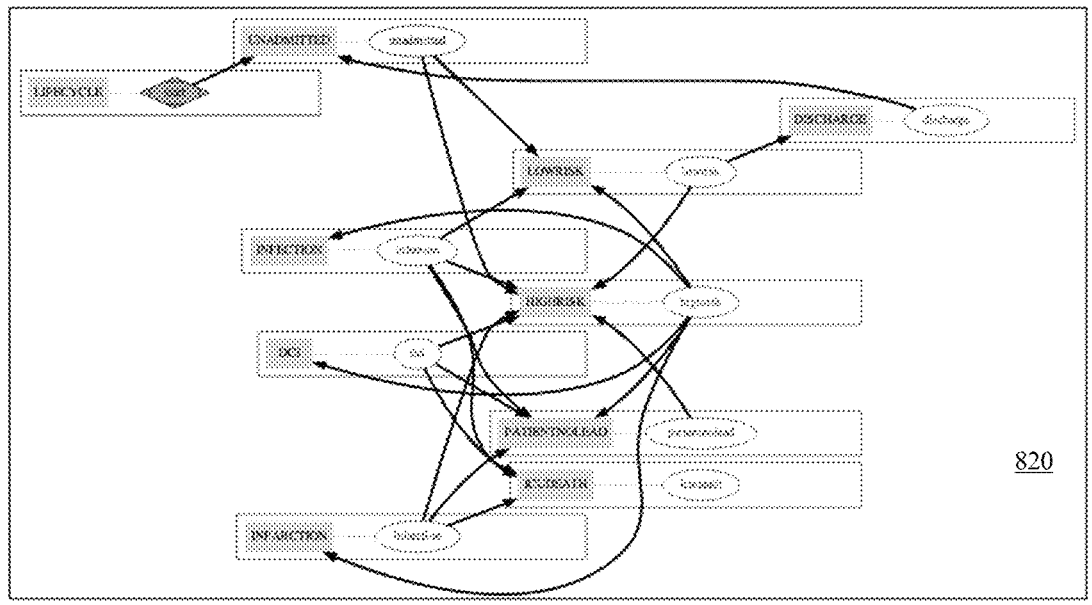
FIG. 8 illustrates an example interface for use as part of at least one embodiment according to the invention.
Figure 11C:
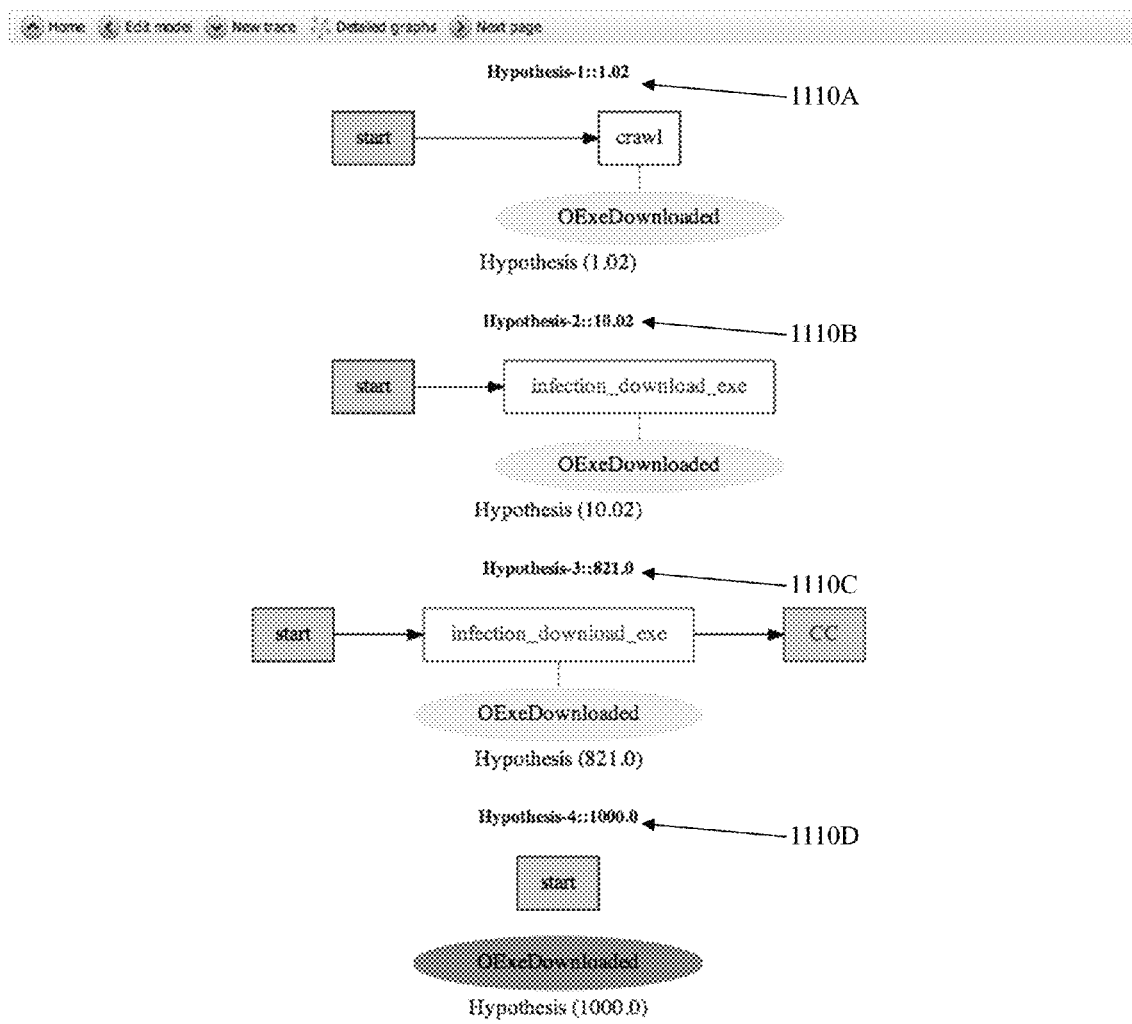
Figures 11D, 12A:
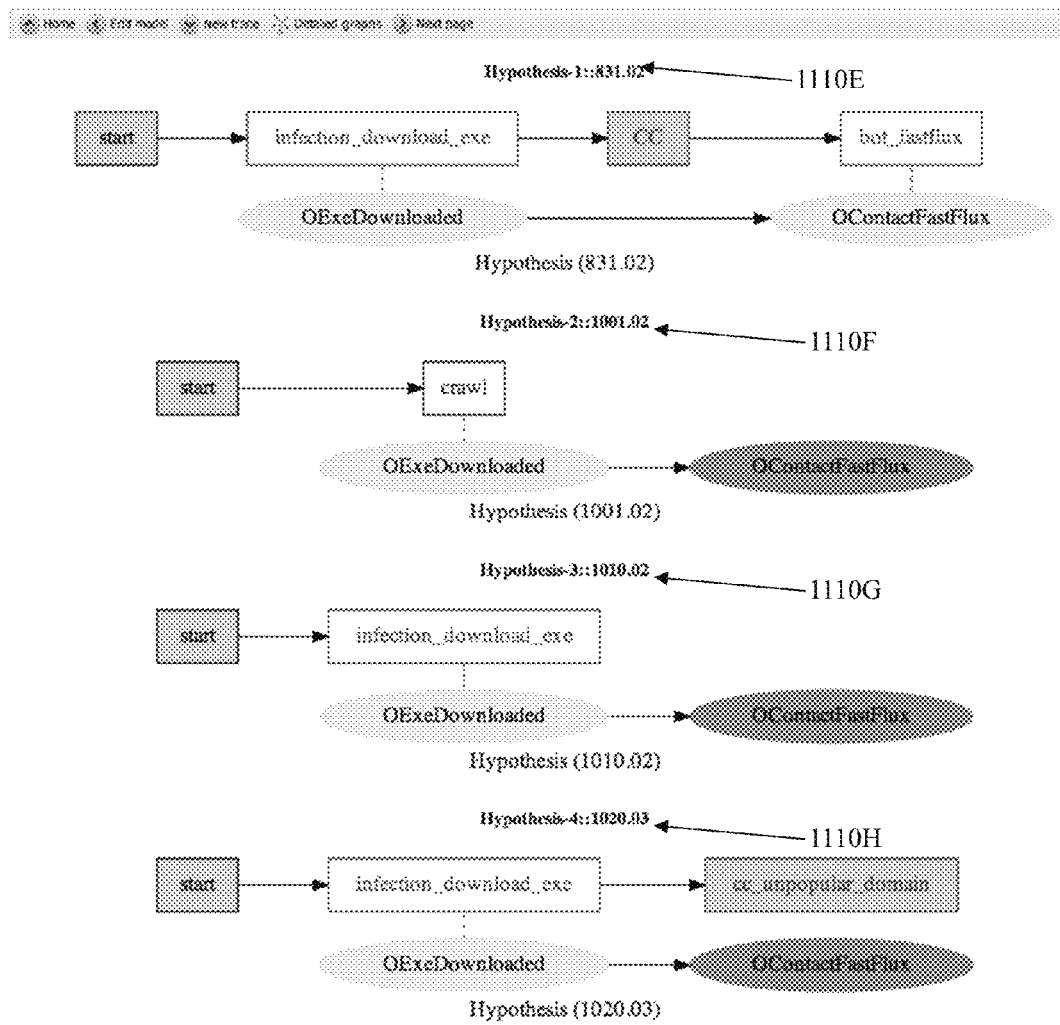

The system in at least one embodiment includes an LTS++ editor 810 illustrated in FIG. 8, graphical view of the transition system 820 illustrated in FIG. 8, specification of the trace, and generation of hypotheses like that illustrated in, for example, FIGS. 11C and 11D. The system automatically generates planning problems from the LTS++ specification and entered trace. The generated hypotheses are the result of running a planner to obtain a set of plans and presenting them as the top-most plausible hypothesis to the least plausible hypothesis. In an alternative embodiment, a plurality of planners is used.

The top part of the interface includes a LTS++ language editor 810, which allows syntax highlighting, and the bottom part is the automatically generated transition graph 820. The transition graph can be very useful for debugging purposes. In a further embodiment, the system also provides error detection with respect to the LTS++ syntax in window 830. The errors and warning signs are provided, for example, in a window 830 below the text editor 810. They too can be used for debugging the model of the system during its creation, 640.

The method in at least one embodiment includes testing of the model, 645.

Figure 7:
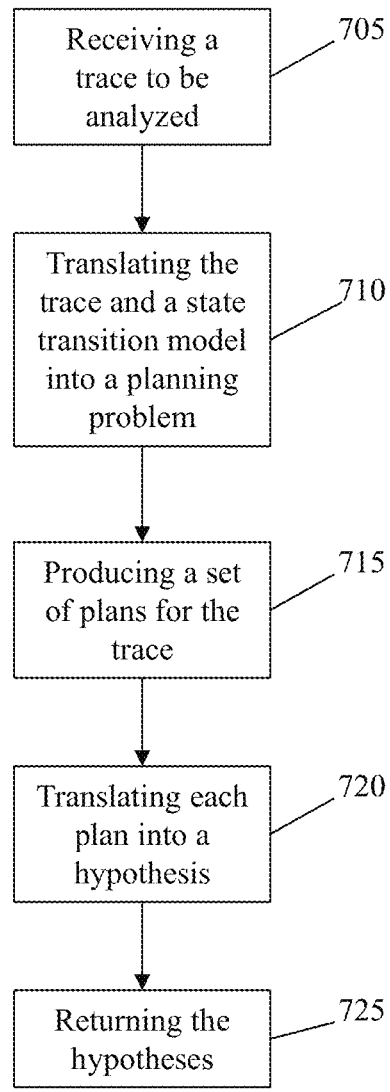
FIG. 7 illustrates a method of at least one embodiment according to the invention.

FIG. 7 illustrates a method for generating hypotheses using an existing model, which may have been created, for example, using the above-described method. Receiving into the system (e.g., the hypothesis generator) from a source a trace to be analyzed, 705. Examples of the source include, but are not limited to, a user, surveillance or monitoring software, medical sensors, electronic medical records system, sensors, etc. In an alternative embodiment, the system also receives an initial state to be used in the hypotheses generation using the model. In at least one embodiment, the trace includes a sequence of observations, and in at least one further embodiment the trace includes at least one past or future observation including one or more of each type.

The system translates the trace and a state transition system (or state transition model) into a planning problem, 710. The state transition system in at least one embodiment is reusable for multiple traces, and as such may be entered into the system independent of the trace and stored, for example, in memory for retrieval by the system. In an alternative embodiment, the state transition system is received by the system proximate the time of receipt of the trace. In at least one further embodiment, the planning problem also includes a planning domain and a planning problem that together with the state transition system define a model of the system that in at least one embodiment is created through a model IDE, which an example is illustrated in FIG. 8. In at least one embodiment, the model uses the LTS++ language.

The system then uses the planner to produce top-k plans for the trace, 715. In an alternative embodiment, the planner finds top-quality or plans that provide the most plausible hypotheses. The system (e.g., the hypotheses generator) then translates each plan into a hypothesis, 720. The system (e.g., the hypotheses generator) then returns the hypotheses, 725.

In an alternative embodiment, the system (e.g., the planner) scores each hypothesis, which in at least one further embodiment allows for ordering the hypotheses based on this scoring, which is based on the calculated plan costs for the plans returned by the planner. In this alternative embodiment, the system provides the resulting list of hypotheses ordered, for example, by the lowest score first. In at least one embodiment, the scores for the hypotheses are based on the scoring of the individual plans by the planner.

In at least one embodiment the returning of the hypotheses includes the system providing the resulting list of hypotheses graphically to the user including the observations entered as part of the trace along with the states included as part of each displayed hypothesis. In a further embodiment, the displayed hypotheses will include linkages between the observations and states (or hyperstates). In further embodiments as illustrated in, for example, FIGS. 11C and 11D the information displayed includes the score (1110A-1110H) for each hypothesis along with a label identifying the hypotheses. The system scores the found hypothesis (plan Ps) based on predetermined characteristics such as "good state", "bad state", most probable, etc. In an alternative embodiment, the method discussed in conjunction with FIG. 9 is used.

In an alternative embodiment, the system sends notifications to appropriate individuals as part of providing information to request further information (i.e., observations) or to alert of potential problems.

Hypothesis generation via planning includes a dynamical system that is defined as $\Sigma=(F; A; I)$, where F is a finite set of fluent symbols, A is a set of actions with preconditions and effects that describes actions that account for the possible transitions of the state of the entity (e.g., patient or host) as well as the discard action that addresses unreliable observations by allowing observations to be unexplained, and I is a clause over F that defines the initial state. The instances of the discard action add transitions to the system that account for leaving an observation unexplained. The added transitions in at least one embodiment ensure that all observations are taken into account but an instance of the discard action for a particular observation o indicates that observation o is not explained. Actions can be over both "good" and "bad" behaviors. This maps to "good" and "bad" states of the entity, different from a system state (i.e., set of fluents over F).

An observation formula $\phi$ is a sequence of fluents in F referred to as a trace. Given the trace $\phi$, and the system description $\Sigma$, a hypothesis $\alpha$ is a sequence of actions in A such that $\alpha$ satisfies $\phi$ in the system $\Sigma$. In at least one embodiment, a notion of plausibility of a hypothesis is defined. Given a set of observations, there are many possible hypotheses, but some could be stated as more plausible than others. For example, since observations are not reliable, the hypothesis $\alpha$ can explain a subset of observations by including instances of the discard action. However, a hypothesis that includes the minimum number of discard actions is more plausible can be indicated. In addition, observations can be ambiguous: they can be explained by instances of "good" actions as well as "bad" actions. Similar to the diagnosis problem, a more plausible hypothesis ideally has the minimum number of "bad" or "faulty" actions. More formally, given a system $\Sigma$ and two hypotheses $\alpha$ and $\alpha'$ as assumption that the system $\Sigma$ can have a reflexive and transitive plausibility relation $\leq$, where $\alpha \leq \alpha'$ indicates that a is at least as plausible as a: In an alternative embodiment, the system is biased towards favoring "bad" actions over "good" actions. In yet a further alternative embodiment, there is no bias between "good" actions and "bad" actions.

The hypothesis generation problem may then be defined as $P=(F, A', I, \phi)$ where A' is the set A with the addition of positive action costs that accounts for the plausibility relation $\leq$. A hypothesis is a plan for P and the most plausible hypothesis is the minimum cost plan. That is, if $\alpha$ and $\alpha'$ are two hypotheses, where $\alpha$ is more plausible than $\alpha'$, then $cost(\alpha) < cost(\alpha')$. Therefore, the most plausible hypothesis is the minimum cost plan. This planning problem has complete information about the initial state, it is deterministic, it deals with temporally extended goals (i.e., the observations are not over a final state), and actions have costs associated with them. The unreliability of observations in this formulation means in at least one embodiment the generation of multiple highly plausible hypotheses (and not simply the most plausible).

The problem of generating hypotheses is closely related to the diagnosis of dynamical systems. There are several approaches to addressing this problem including SAT-based and planning-based approaches. In at least one embodiment, there is no assumption that the observations are perfect and not just a single plausible hypothesis is found, but a set of most plausible hypothesis so that they can be further refined by testing.

In at least one further embodiment, the plausibility notions are encoded as action costs. In particular, a high action cost is assigned to the "discard" action in order to encourage explaining more observations. In addition, a higher action cost is assigned to all instances of the actions that represent malicious behaviors than those that represent non-malicious behaviors (this is relative that is if a action cost of 20 is assigned to a malicious action instance, then an action cost less than 20 is assigned to all other non-malicious action instances). Also actions that belong to the same lifecycle state can have different costs associated with them. This is because not all actions are equally likely and can have the same weight in determining the root cause. However, there could be additional knowledge that indicates a more plausible root cause. For example, if two observations are indicated, a download from a blacklisted domain and download an executable file, the system could indicate that an infection is more likely if downloading from a blacklisted domain. This can be achieved by assigning a higher cost to the action that represents infection by downloading an executable file than the action that represents downloading from blacklisted domain.

In at least one embodiment, the method exploits LAMA (see, e.g., Richter et al., "The LAMA Planner: Guiding Cost-Based Anytime Planning with Landmarks", Journal of Artificial Intelligence Research, Vol. 39, 2010, pp. 127-177), which is an example of a PDDL planner, to generate multiple distinct high-quality plans, because unreliable observations exist in the world. LAMA is an incremental planner, meaning that it continues to find plans with increasing quality until a time limit is reached. So it generates a sequence of plans within the given time limit. The last plan it finds is the best one or the optimal plan. However, the other plans that it finds may not necessarily be good quality plans. LAMA is used in at least one embodiment to perform multiple replanning phases in order to generate multiple high-quality plans. In at least one alternative embodiment, another planner is used to generate hypotheses.

Given a description of a planning problem, a need exists to generate multiple high-quality (or, equivalently, the low-cost) plans, each corresponding to a distinct plausible hypothesis.

In at least one embodiment, the planning domain is extended by associating a new unique predicate with each action, and including every parameter of the action in the predicate. By adding this predicate to the effect of the action, and its negation, with specific parameter values, to the goal, a specific instance of an action can be prevented from appearing in the plan.

In a further embodiment, a replanning process uses LAMA to generate multiple high-quality (or low-cost) plans that correspond to a set of plausible hypothesis. The replanning process works in such a way that after each round, the planning problem is updated to disallow finding the same set of plans in future runs of LAMA. In a further embodiment, the process continues until a time limit is reached and then all found plans are sorted by plan cost and shown to the user via a display interface, for example, ten hypotheses per page. In a further alternative embodiment, the process continues until a predetermined number of plans are found. Or in an alternative embodiment, the time limit and predetermined number are used together to end the process when the first is reached or after both have been reached. These are examples of predetermined thresholds.

The observations in at least one embodiment are considered to be temporally extended goals. When a classical planner is used, first the system compiles observations. In at least one embodiment, instead of having an "advance" action that ensures the observation order is preserved, each action that emits an observation has an ordering precondition. Hence, only a "pending" observation can be observed, and upon doing so, the next observation becomes pending. This ensures that the generated plans meet the observations in exactly the given order.

To drive the replanning process in at least one embodiment, a wrapper is implemented around the planner. A method for the wrapper is illustrated in FIG. 9 as pseudo-code. The wrapper first generates an optimal or near-optimal plan using an unmodified problem P, 0. It then modifies the problem P to exclude the specific action instances of the first plan one by one, 1, and generates a near optimal plan for each modification, 5. The wrapper then recursively applies this procedure to each plan from the new set, 1-9, this time excluding both the action from the new plan, and the action that was excluded from the first plan when generating the new plan, 1. The process in at least one embodiment continues until a preset time limit is reached. In an alternative embodiment, a time limit can be specified for each planner invocation (each iteration of the planner), to ensure a minimum of modified goals explored. In general the number of excluded actions is equal to the depth of the search tree the algorithm is traversing in a breadth-first manner. The replanning method in at least one embodiment can eventually find every valid plan if used with a complete planner and given enough time.

In at least one implementation, a subset of actions sufficient for generating different plans is used. Action sets are sorted, 2, for example, so that the instances of the discard action are removed before other actions. Finally, all plans are stored (or saved), if multiple plans are generated by the planner during one round. In at least one further embodiment, only one best generated plan is used to generate new action sets.

This process generates multiple distinct plans, and therefore hypotheses. After sorting them by plan cost, a subset can be presented to administrators or automated systems as possible hypotheses for future investigation.

In a further embodiment, returning a set of plans includes finding at least one plan P using the trace and at least one planner. In different embodiments, the set of plans includes one or more of top-quality plans, plans producing the most plausible hypotheses, and top-k plans. Eliminating at least one state from the found plan P and finding a new plan $P_n$, where n is the iteration of that found plan. Repeating the iterations until a predetermined threshold has been reached. In at least one embodiment, the predetermined threshold is at least one of a predetermined time or a predetermined number of plans are located.

An alternative planner to LAMA is MARIO, which was developed by International Business Machines Corp. (IBM) to find top-K hypotheses. MARIO is a specialized planner, proposed to work with the composition pattern language Cascade to generate plans for the automated composition task (e.g., stream processing).

Applications

As mentioned previously, two example applications of the above described systems and methods are network traffic analysis (or malware detection) or proactive patient care in an ICU setting (or health care). In the following paragraphs, an overview of these applications will be provided and examples of how the use of the above described systems and methods would work with these example applications.

The first example application is hypothesis generation for network traffic analysis.

Consider the case of enterprise network monitoring. Although such networks are typically equipped with state-of-the-art security appliances and firewalls, these devices and software are designed to look for known signatures of cyber threats by examining very small windows of data, for example, one Transmission Control Protocol (TCP) session. Most modern malware such as bots uses techniques for disguising its network communications in normal traffic over time. For effective malware detection, techniques examine observations of network traffic over a longer period of time and produce hypotheses on whether such traces correspond to a malware lifecycle or otherwise innocuous behavior. Practically, since any such hypothesis has a degree of uncertainty, it must be presented in a form that explains how observed behavior indicates either malware or other lifecycles of network activity.

As an example, a (simplified) malware lifecycle could be illustrated like the illustration in FIG. 10. The rectangles on the left side correspond to malware lifecycle states, such as the host becoming infected with malware, the bot's rendezvous with a Command and Control (C&C) machine (botmaster), the spread of infection to neighboring machines and a number of exploits—uses of the bot for malicious activity. Each of the lifecycle states can be achieved in many ways depending on the type and capabilities of the malware. For example, C&C Rendezvous can be achieved by attempting to contact an Internet domain, via Internet Relay Chat (IRC) on a dedicated channel, by contacting an infected machine acting a local C&C, or by Peer-to-Peer (P2P) traffic with a preset IP address. In FIG. 10, the right-most nodes (excluding Crawling) are observations derived from network data that could be obtained in the corresponding lifecycle states. As an example, NX volume corresponds to an abnormally high number of domain does not exist responses for Domain Name System (DNS) queries; such an observation may indicate that the bot and its botmaster are using a domain name generation algorithm, and the bot is testing generated domain names trying to find its master. On the right side of FIG. 10, a "normal" lifecycle of a web crawler compressed into a single state is depicted as "Crawling". Note that crawler behavior can also generate a subset of the observations that malware may generate. Although this is a small example, it can be extended by adding more known lifecycles, expanding the number of observations covered, introducing loops (e.g., having a periodic C&C Rendezvous after exploits), etc. Furthermore, the lifecycle graph can be used to model infection propagation—e.g., by linking the Infect Neighbor state for host A to Infection—Neighbor for host B (e.g., if A is port-scanning B for vulnerabilities).

In the lifecycle, observations are the result of performing analysis on network data. The NX volume observation for instance is the result of modeling the typical number of negative responses to DNS queries, aggregating DNS data for a window of time for a host and determining if its NX response volume is an outlier. While the complexity of the analysis involved to obtain one observation can vary, it is important to note that observations are by nature unreliable because of multiple reasons including those described in the following paragraphs.

The set of observations will likely be incomplete. Operational constraints will prevent running in-depth analysis on all the network traffic all the time. However, all observations are typically time-stamped and hence totally ordered.

Observations may be ambiguous as illustrated in FIG. 10, where for instance contacting a blacklisted domain may be evidence of malware activity or maybe a crawler that reaches such a domain during normal navigation.

Observations may be mutually inconsistent as occurs when observations that can be explained by mutually exclusive lifecycle paths—e.g., observations that are exclusive to the malware lifecycle and observations that are exclusive to crawling behavior in the same sequence.

Not all observations will be explainable. There are several reasons why some observations may remain unexplained: (i) in this setting observations are (sometimes weak) indicators of a behavior, rather than authoritative measurements; (ii) the lifecycle description is by necessity incomplete, unless it is possible to model the behavior of all software and malware; (iii) there are multiple processes on a machine using the network, making it difficult to determine which process originated which behavior; and (iv) malware throws off security scans by either hiding in normal traffic patterns or originating extra traffic to confuse detectors.

An example includes two observations for a host: ($o_1$) a download from a blacklisted domain and ($o_2$) an increase in traffic with ad servers. Note that according to FIG. 10, this sequence could be explained by two hypotheses: (a) a crawler or (b) an infection by downloading from a blacklisted domain, a C&C Rendezvous which would be unable to be observed, and an exploit involving click fraud. In such a setting, it is normal to believe (a) is more plausible than (b) since we have no evidence of a C&C Rendezvous taking place. However, take the sequence ($o_1$) followed by ($o_3$) an increase in IRC (Internet Relay Chat) traffic followed by ($o_2$). In this case, it is reasonable to believe that the presence of malware—as indicated by the C&C Rendezvous on IRC—is more likely than crawling, since crawlers do not use IRC. The crawling hypothesis however cannot be completely discounted since it may well be that a crawler program is running in the background, while a human user is using IRC to chat.

Due to the unreliability of observations, in order to address the malware detection problem a technique is needed that considers a sequence of observations and produces not just one, but a ranked list of hypotheses (explanations of the observations), such that: (i) some hypotheses may ignore (leave as unexplained) observations that are deemed unreliable or inconsistent and (ii) the rank of the hypothesis is a measure of their plausibility. Since the number of observations in practice can grow into the tens or hundreds for even such small lifecycle descriptions, having a network administrator manually create such a ranked list is not a scalable approach. As described above in at least one embodiment, the system uses planning to automatically sift through hundreds of competing hypotheses and find multiple highly plausible hypotheses. The result of the automated technique can then be presented to a network administrator or to an automated system for further investigation and testing. In at least one embodiment, the automated technique uses automated AI planning.

Using this example application, the disclosure will define a simple lifecycle in LTS++ for it.

The state machine is defined by defining states, transitions, observations and state types. An example is illustrated in FIG. 11A. The all-caps identifiers such as "INFECTION" represent hyperstates. Each state (such as reading shared disk) can be only used within one hyperstate. Observations (or, more precisely, observation types which are the items beginning with "O"), such as OReadSharedDisk, are associated with states by listing them immediately after the state in curly brackets, and in at least one further embodiment are automatically defined on first use. The same observation can be associated with multiple states, and each state may have multiple observations associated with it.

Each state can be associated with one of the state types. The set of state types is determined by a configuration file (planning domain for hypothesis generation), and in the current configuration includes good state and bad state, as well as preferences in ambiguous cases between good state explanations to bad state explanations.

The default-class statement specifies the default state type for states. The starting statement can specify a list of states that are allowed to appear at the beginning of the trace.

FIG. 8 illustrates an example interface that may be used to enter the observations into a model such as the LTS++ lifecycle specified above, one could create the following trace or list of observation types: "OReadSharedDisk OPortScan". This trace has some missing observations since it skips over the "INFECTION" and "CC" hyperstates, and the generated hypotheses will either discard observations or allow unobserved transitions through hyperstates (i.e., representing the hypothesis that the infection and command-and-control stages did not have states that are observable in our model, and a previously unknown attack was used).

FIG. 11B illustrates an example of the encoding of the malware detection problem illustrated in FIG. 10 in LTS++.

FIG. 11C illustrates the top 4 hypotheses provided by the system when the trace "OExecDownload" was received by it.

In at least one embodiment, the display interface will show ten hypotheses per page, and allow the user to navigate through pages to get the next set of ten hypotheses. The shown hypotheses are ranked in at least one embodiment based on their plausibility values. That is the top one (the one with the lower number) is the most plausible hypothesis. Based on this disclosure, it should be understood that other numbers of hypotheses could be displayed on each page.

FIG. 11D illustrates another example run of the system. The trace is "OExecDownload" followed by "OContactFastFlux". For illustration purposes just the first four hypotheses are illustrated.

In at least one embodiment, the malware detection model is extended so that we can generate possible future. For this example, the model is extended by adding "OFuture" observation types to each state where there is an interest (which could be all of them), and adding several "OFuture" observations to the trace.

FIG. 12A illustrates how the lifecycle introduced earlier in FIG. 11A may be modified to include multiple "OFuture"s.

The following sample trace will generate multiple possible future scenarios: "OReadSharedDisk OFuture OFuture". The number of OFuture observations added to the trace corresponds to the number of future observations that should be predicted, and in most cases looking two or three steps ahead is sufficient.

FIG. 12B illustrates one approach for how the malware detection problem illustrated in FIG. 11B was modified to address future states.

FIG. 12C illustrates some interesting hypotheses returned by the system for the following trace on this updated model: "OExeDownload OIncreaseInIRC OFuture OFuture".

In an a further embodiment and similar to the use of future observations, hypotheses about possible events in the past, i.e., alternative histories, can be generated by inserting several "OPast" observations at the beginning of the trace, and updating the model to have "OPast" instead of "OFuture" as follows: "OPast OPast OPortScan". The example above will generate possible scenarios that could have led to a port scan observation.

Figures 12D, 13B:
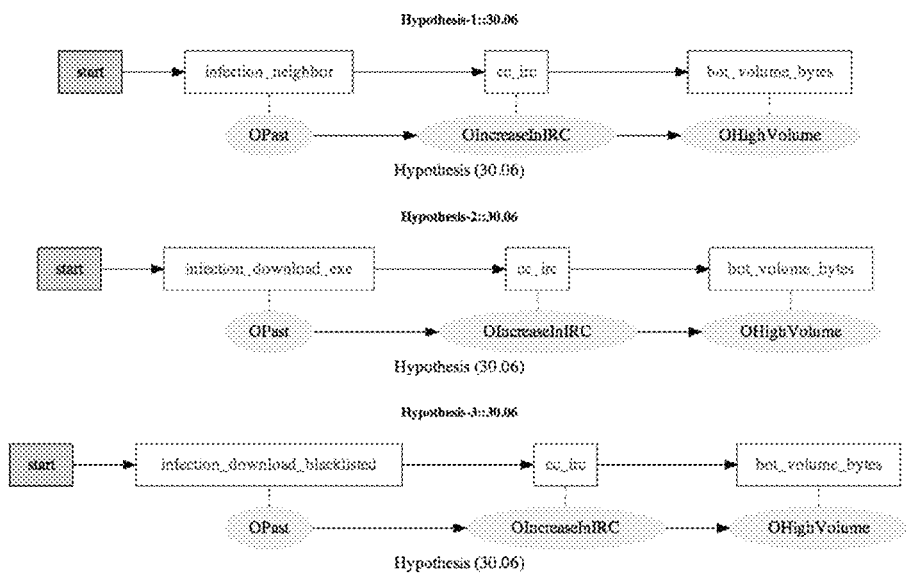
FIG. 12D illustrates hypotheses about possible events in the past based on the modified model illustrated in FIG. 12B where OFuture is replaced with OPast.
FIG. 13B illustrates an example of defined states, transitions, observations and state types for FIG. 13A.

FIG. 12D illustrates the first three hypotheses for the trace: "OPast OIncreaseInIRC OHighVolume". In at least one embodiment, the system considers possible alternative histories or explanations for "OPast".

Figure 12F:
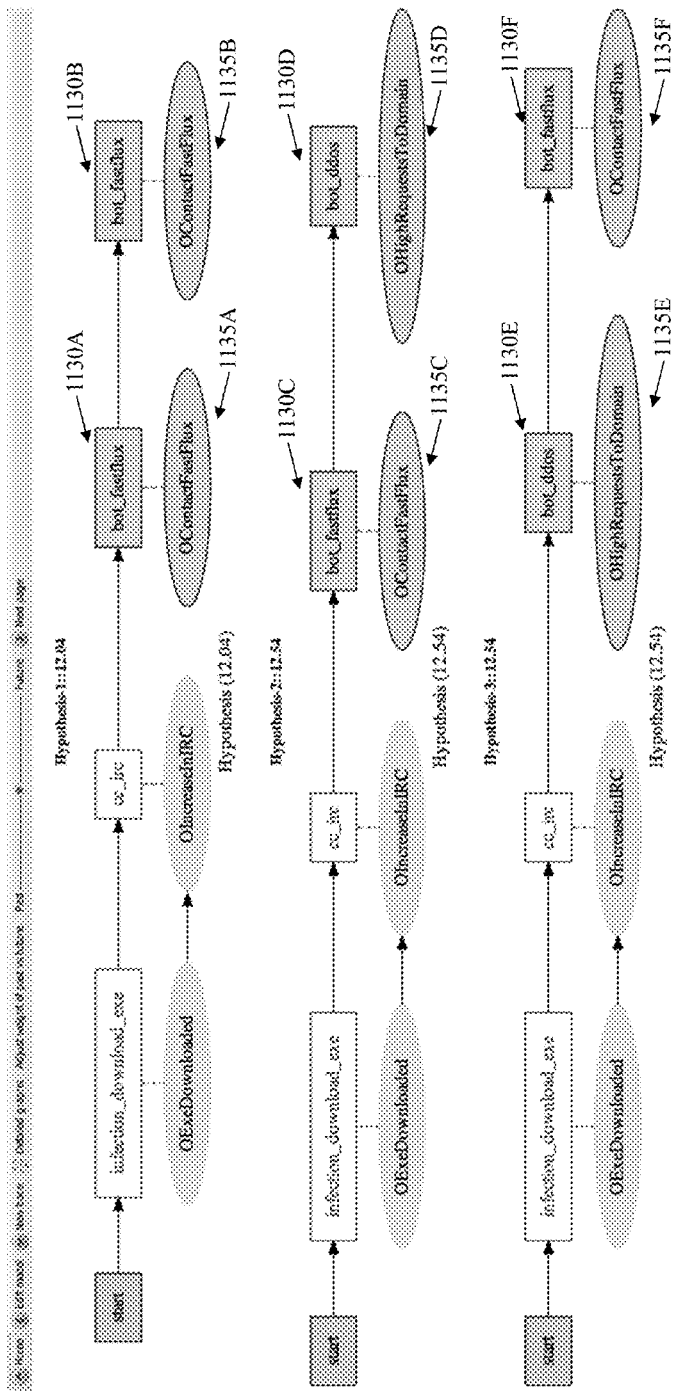
FIG. 12F illustrates hypotheses generated based on FIG. 12E.

FIG. 12E illustrates another approach for how the malware detection problem can be encoded so that we can generate possible futures. For this example, the model is not extended by adding "OFuture" observations. Here instead of adding several "OFuture" observations to the trace, the user can enter a number of Future Steps that the system needs to consider and the system generates the hypotheses accordingly (see, for example, the interface illustrated in FIG. 14D). FIG. 12F shows the hypotheses generated for the trace "OExeDownload OInreaseIRC" where the user enters two for the future steps. The future states are shown in the shaded boxes 1230A-1230F. The observations in the ovals 1235A-1235F are observations "to look for" and are associated with the future states.

FIG. 13B illustrates another example of a LTS++ model for the malware detection from FIG. 13A. The states are the labels without a starting "O" with hyperstates specified in all caps. The observations are specified within the curly brackets and start with "O". In at least one embodiment, it is possible to specify multiple observations by using space between observations (see line 6). The state types are specified within angle brackets (see line 2). The transitions between statutes are specified using arrows. Each transition needs to be specified within a hyperstate. Multiple transitions between states within a hyperstate can be specified using the vertical bar. The default state types in specified in line 1 and the starting state must be specified in the last line.

For illustration purposes, an explanation of how observations can be entered into the system in at least one embodiment is provided below.

Figure 14A:
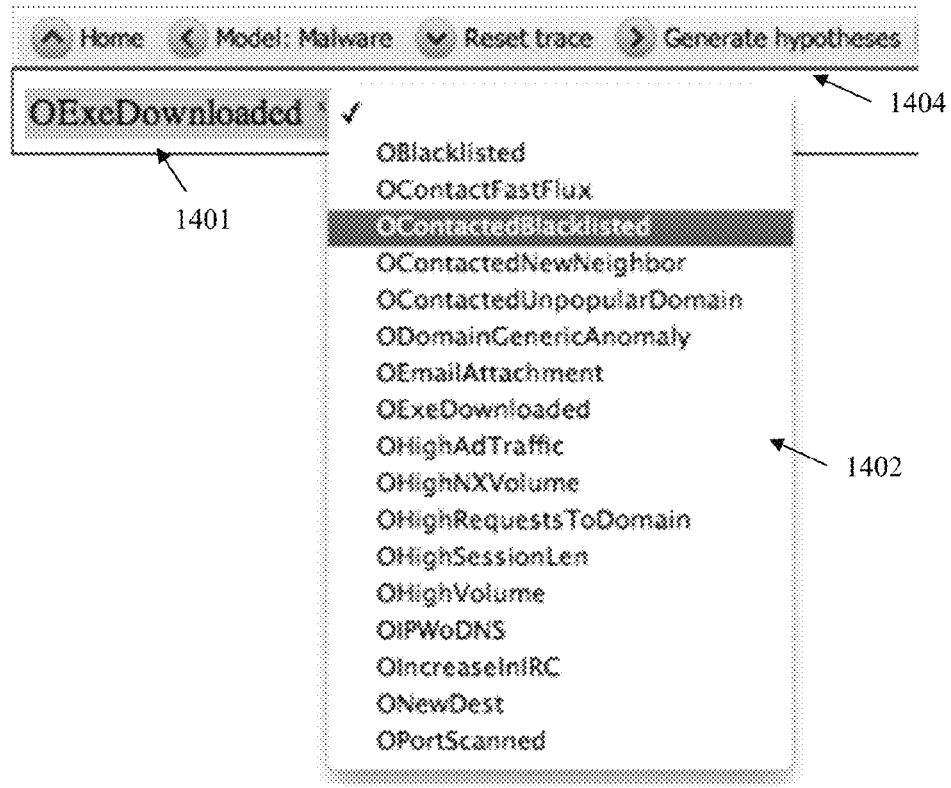
FIG. 14A illustrates an example interface for use in entering a trace in at least one embodiment according to the invention.

Observations can be entered by clicking on the "Next: edit trace" 842 from the system main page illustrated in FIG. 8. FIG. 14A illustrates an example of an interface for entering a trace using drop-down menus. An alternative method for entering data is the use of text files, text or other data files. In the illustrated example, the first observation is selected to be the executable download 1401 and the second observation is now being selected from the drop-down menu 1402. Once the trace selection is complete, the hypotheses can be generated by clicking on "Generate hypotheses" 1404. The hypotheses are presented to the user through at least one page, and users can navigate through these pages if multiple pages are available. In at least one embodiment, the next set of hypotheses is generated once the user clicks on the "Next page" 1406. In at least one further embodiment, the trace editor illustrated in FIG. 8 is intended mainly for testing purposes and in operation, the system will be configured automatically to an input queue for observations. In at least one embodiment, any clicks or selections by the user (including domain expert) result in a signal or other input to the system to perform the requested action.

Figure 14D:
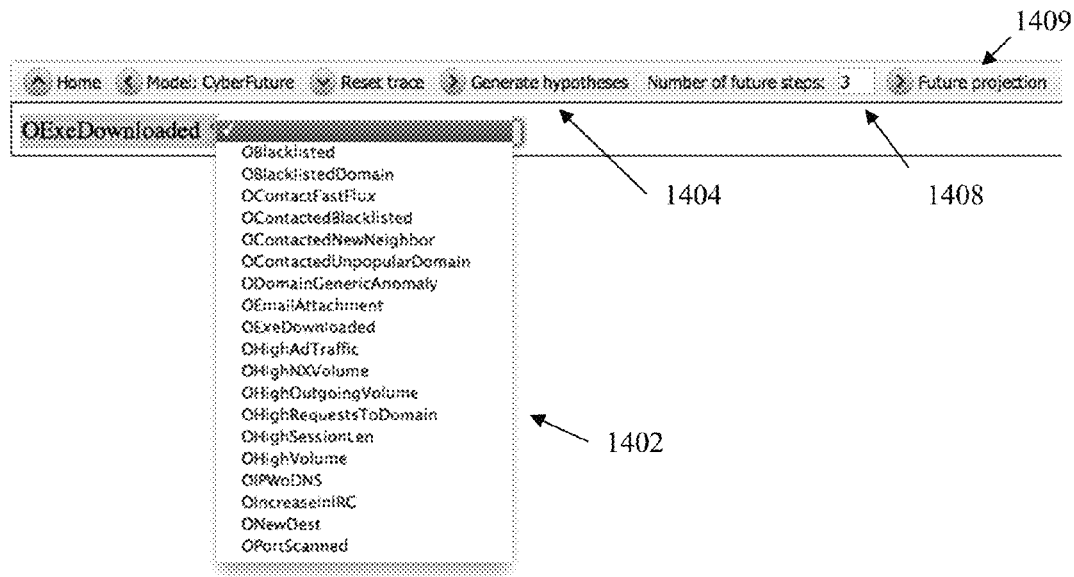
FIG. 14D illustrates another example interface for use in entering a trace in at least one embodiment.
Figure 14B:
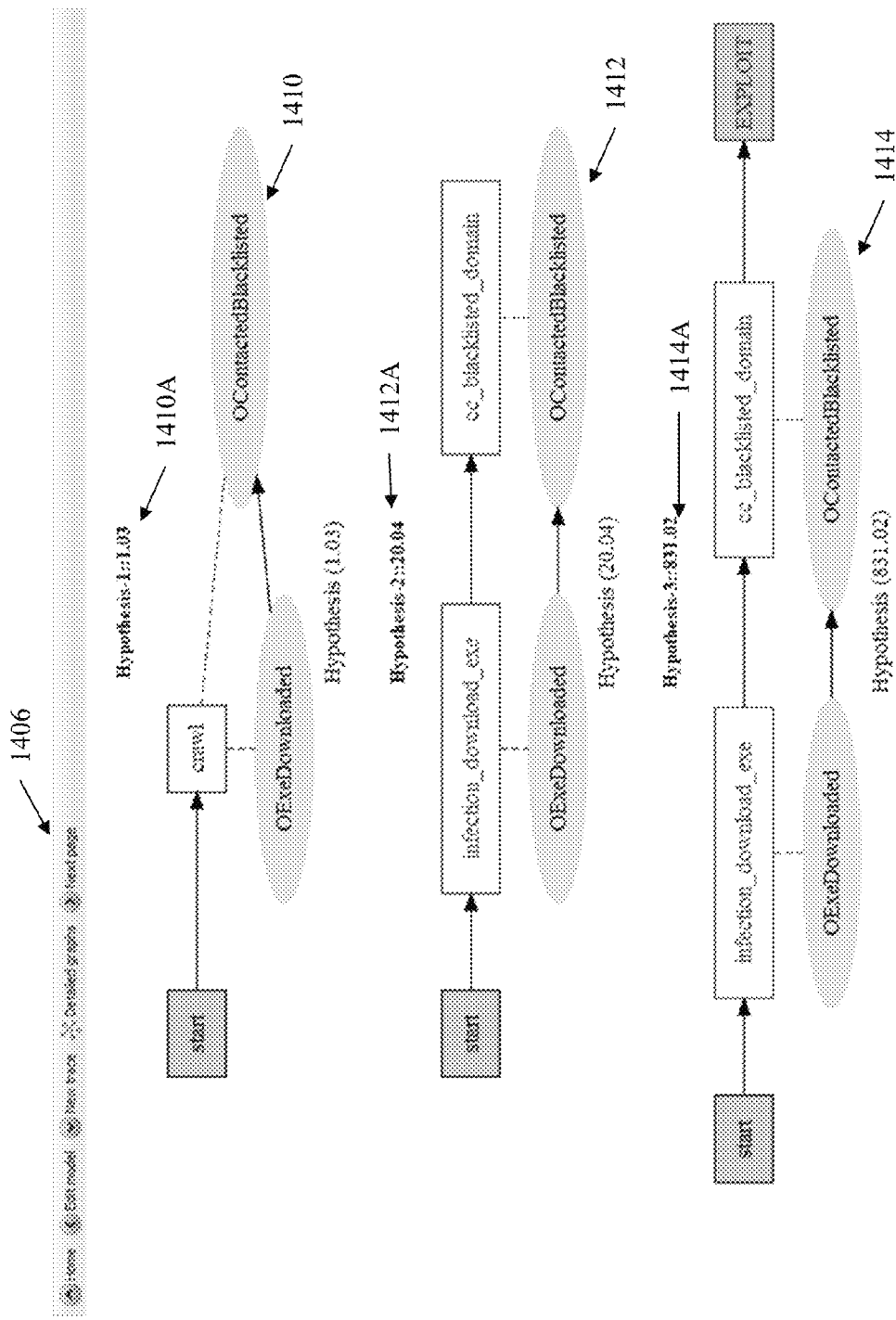
FIGS. 14B and 14C illustrate hypotheses generated based on the trace entered in the example depicted in FIG. 14A.
Figure 14C:
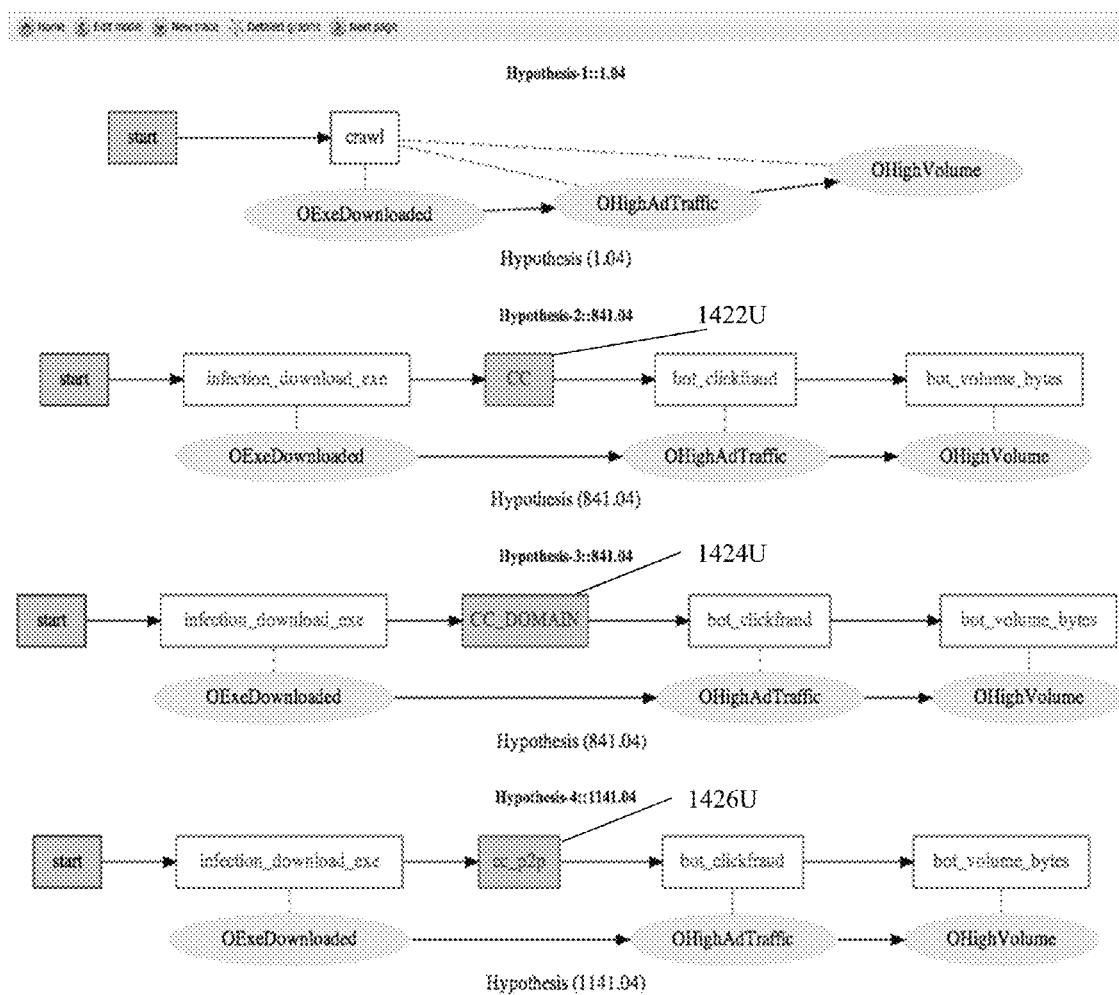

FIG. 14B illustrates the top three generated hypotheses for the trace selected in FIG. 14A. Each hypothesis is shown as sequence of states (boxes) matched to observed event sequence. The observations that are explained by a state are shown in ovals and unexplained observations are shown without a connected state. The dashed lines show the association between states and the explained observations. The arrows between the observations show the sequence of observations in the trace. The first hypothesis 1410 explains both observations. The second hypothesis 1412, almost as plausible based on its score (1412A), shows infection followed by the Command & Control state. The third hypothesis 1414 leaves the second observation ("OContacted-Blacklisted") explained but with the added result of EXPLOIT. Each hypothesis is associated with a score 1410A, 1412A, 1414A. The lower the score, the more plausible is the hypothesis. In some instances, hypotheses include states with no associated observation. For example, the "CC" 1422U, "CC_Domain" 1424U, "cc_p2p" 1426U are the unobserved states in the non-crawling hypotheses in FIG. 14C.

FIG. 14D illustrates an alternative interface for entering a trace using a drop-down menu 1402 that also allows for entry of a fixed number of future steps (field 1408). Once the trace is completed in a further embodiment, the user has the option to generate the future projections by clicking on "Future Projection" 1409. In an alternative embodiment, there is a box for entry of a fixed number of past steps instead of future steps or in addition to future steps.

In a further embodiment with the future states, the future hypotheses are not ranked based on plausibility, but are ranked based on worst-to-best predictive outcome. The user can specify the importance type for a state (e.g., lowest_imp, low_imp, med_imp, high_imp, highest_imp). The high-imp is associated with the worst consequence, whereas the lowest-imp is associated with the best consequence. The future hypotheses are then ranked from worst-to-best outcome. For example, in FIG. 12E the bot_fastFlux is associated with the highest-imp type and as a result in FIG. 12F the hypotheses with bot_fastFlux are shown first.

In another embodiment, future states or past states can be generated in addition to a hypothesis explaining the observations. A specified number of future states can be requested through an interface such as the one illustrated in FIG. 14E. The model is then automatically modified by associating a new unique observation, OFuture, with each state of the original model. The observation trace is also automatically modified, by adding OFuture observations to the end of the trace. The number of OFuture observations added is the same as the number of future states requested. As in the previously described method embodiment, the resulting hypotheses will include the states matched to all observations, including the OFuture observations. States matched to OFuture observations represent possible future states continuing the sequence of state transitions according to the model. For each of the future states, observations associated with those states can be produced and presented as part of hypothesis, to indicate which observations should be monitored in the future. Example of this is illustrated in FIG. 12F where OContactFastFlux is an observation (1235A-1235C, 1235F) associated with a future state "bot_fastflux" (1230A-1230C, 1230F) indicating an observation to "look for" or monitor. In a modification of the above approach, OFuture observations may be added not to every state, but to only several chosen states. This modification can be used to restrict the future hypotheses generated to only those that include the chosen states as possible future states. Past states are generated by following a similar procedure for future states, adding, instead of OFuture, OPast observations to the states of the model. Unlike OFuture observations that are added to the end of the trace, OPast are added to the beginning of the trace.

The second example application is hypothesis generation for proactive patient care in an ICU setting.

The main goal in the healthcare application is the early detection of a patient state in an Intensive Care Unit (ICU) setting of a hospital. There are a variety of measurements captured by patient monitoring devices (in at least one embodiment, these are examples of sensors 502 in FIG. 5), the results of computations done based on these measurements, as well as other measurements and computations provided by doctors and nurses. Some of these measurements are illustrated in FIG. 15A. For example, given the patient's heart rate, their blood pressure, and their temperature, which are measured continuously, a number will be given to the patient. This number, which is between 0 and 4, determines their SIRS factor. Similarly, a result of a CT Scan or a lab test will indicate other possible observations about the patient.

These observations similar to the malware detection application can be unreliable; they can be noisy, missing, or incomplete. Therefore, some observations may be left unexplainable by the model. FIG. 15B illustrates a sample state transition graph for the state of the patient. The patient is first unadmitted and upon admission they are either in low risk or in high risk. From a high-risk state, they may get to the infection, infarction, or the dci state. From low risk they may get to the high-risk state or be discharged from ICU. The patient enters ICU death from infection, infarction, or dci state. The patient's condition may get improve; hence the patient state may move to the high-risk state from infection, infarction, or dci state. FIG. 15C illustrates another view of FIG. 15A that links observations to states shown by the callouts.

Figures 16A, 16B:
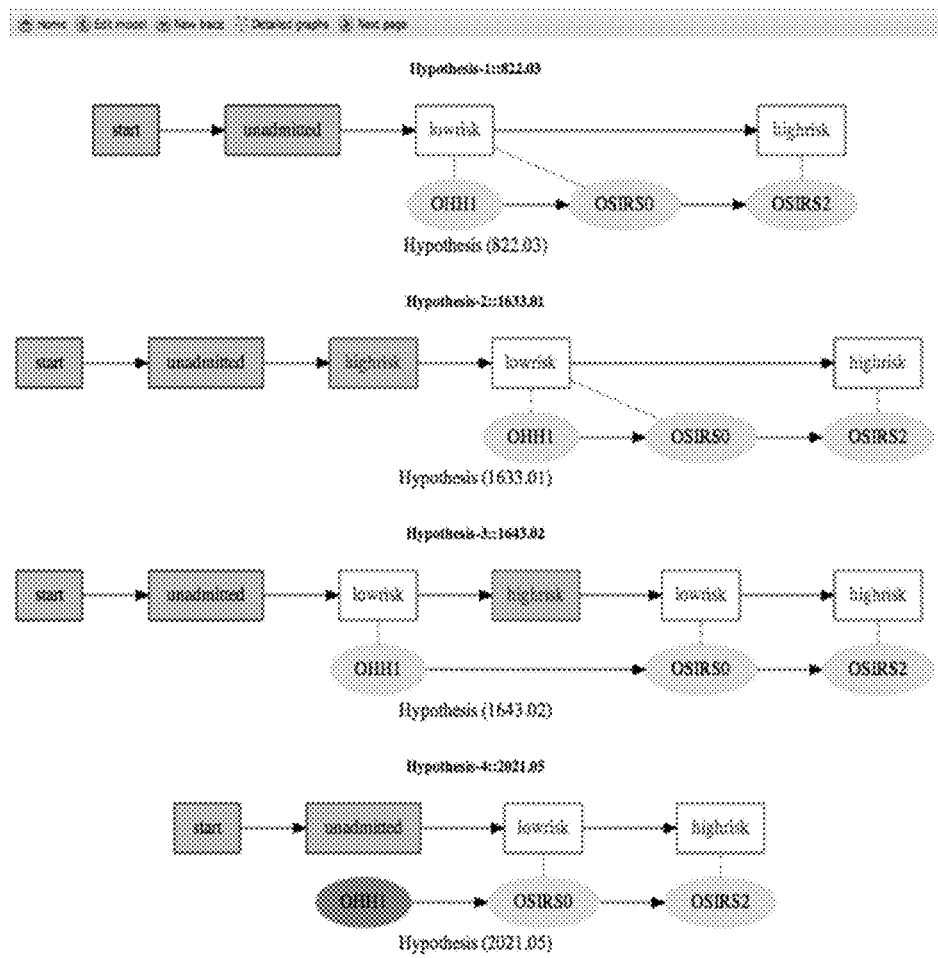
FIG. 16A illustrates an example of defined states, transitions, observations and state types.
FIGS. 16B and 16C illustrate hypotheses generated based on FIG. 16A.

FIG. 16A illustrates an example of the encoding of the healthcare domain in LTS++. Note that there are several transitions to/from the high risk state. Also in the healthcare example there are fewer states, but there are more observation types. Also note that several states can explain the OHRVL, but by gathering more observations or more tests, the hypotheses can further be disambiguated. FIG. 15C shows the state transitions of the healthcare domain together with the association of states and observations using the callouts.

FIG. 16B illustrates the first four hypotheses returned by the system for the following trace: "OHH1 OSIRS0 OSIRS2".

Figure 16C:
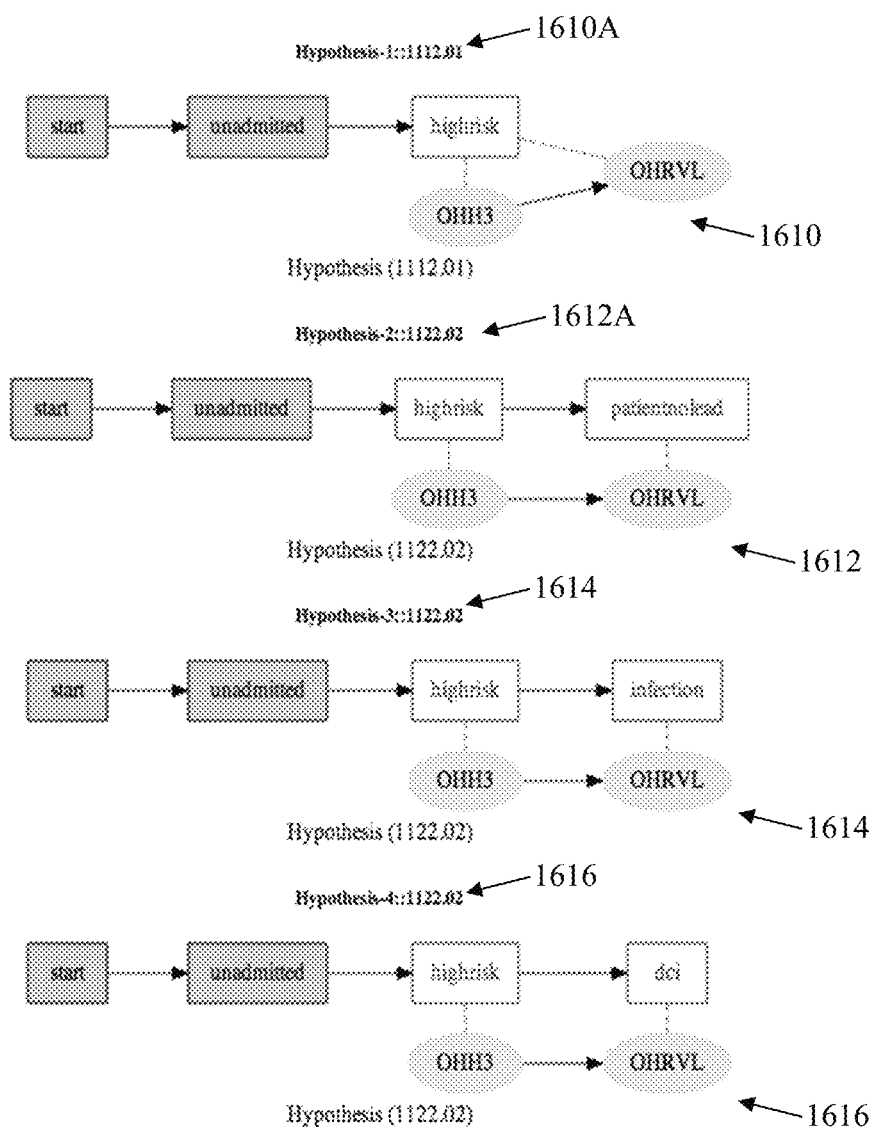

FIG. 16C illustrates another run of the system, this time for the trace: "OHH3 OHRVL". Note that "OHRVL" is an ambiguous observation since it can be explained by more than one state. In particular, the first hypothesis 1610 explains both observations by the highrisk state. But the next three hypotheses 1612-1616 are almost as likely based on their respective scores 1610A-1616A. One can give the system, more observations, to help disambiguate the set of the hypotheses.

Figure 16D:
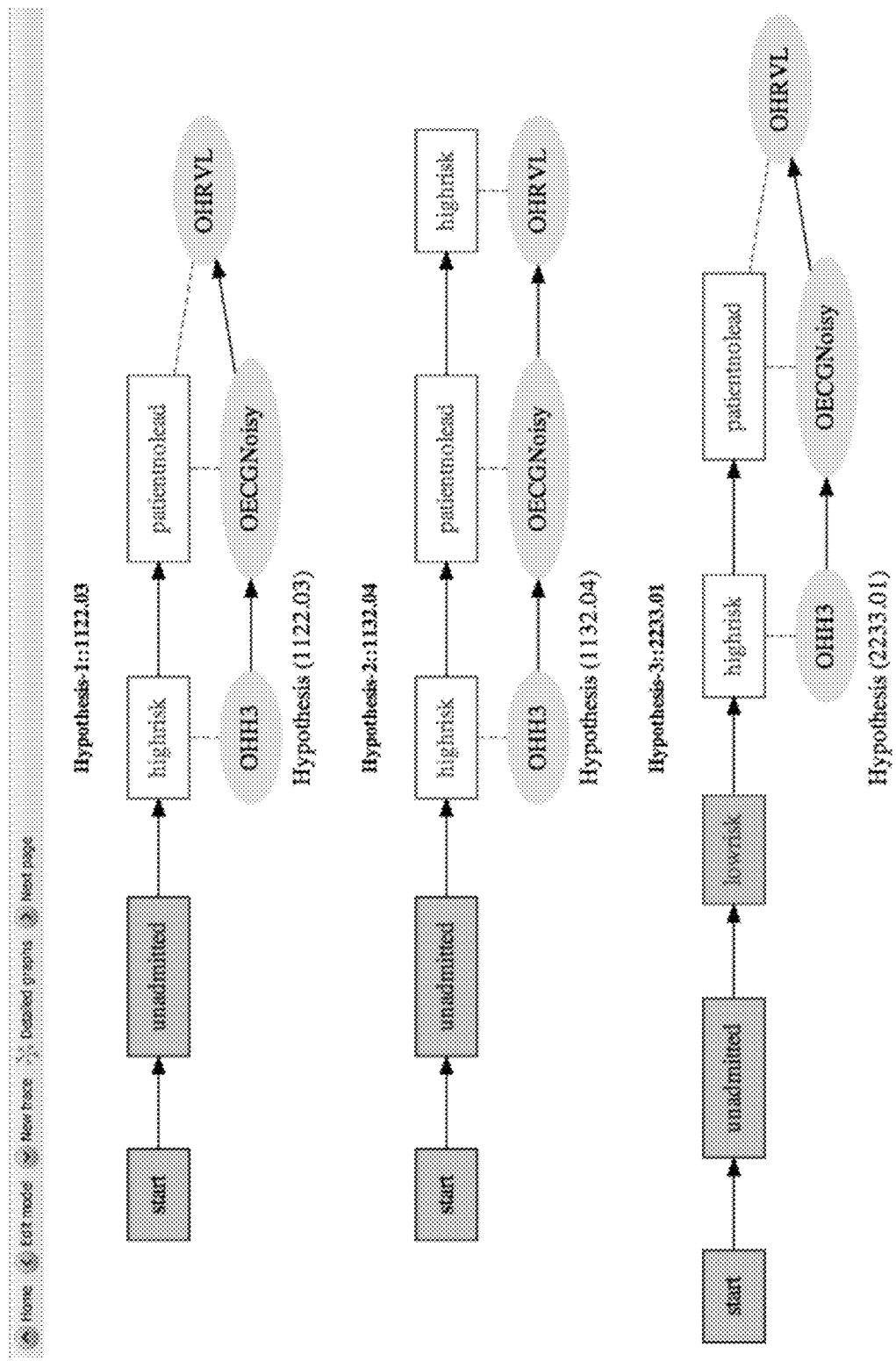
FIGS. 16D and 16E illustrate hypotheses generated for an application of at least one embodiment according to the invention.
Figure 16E:
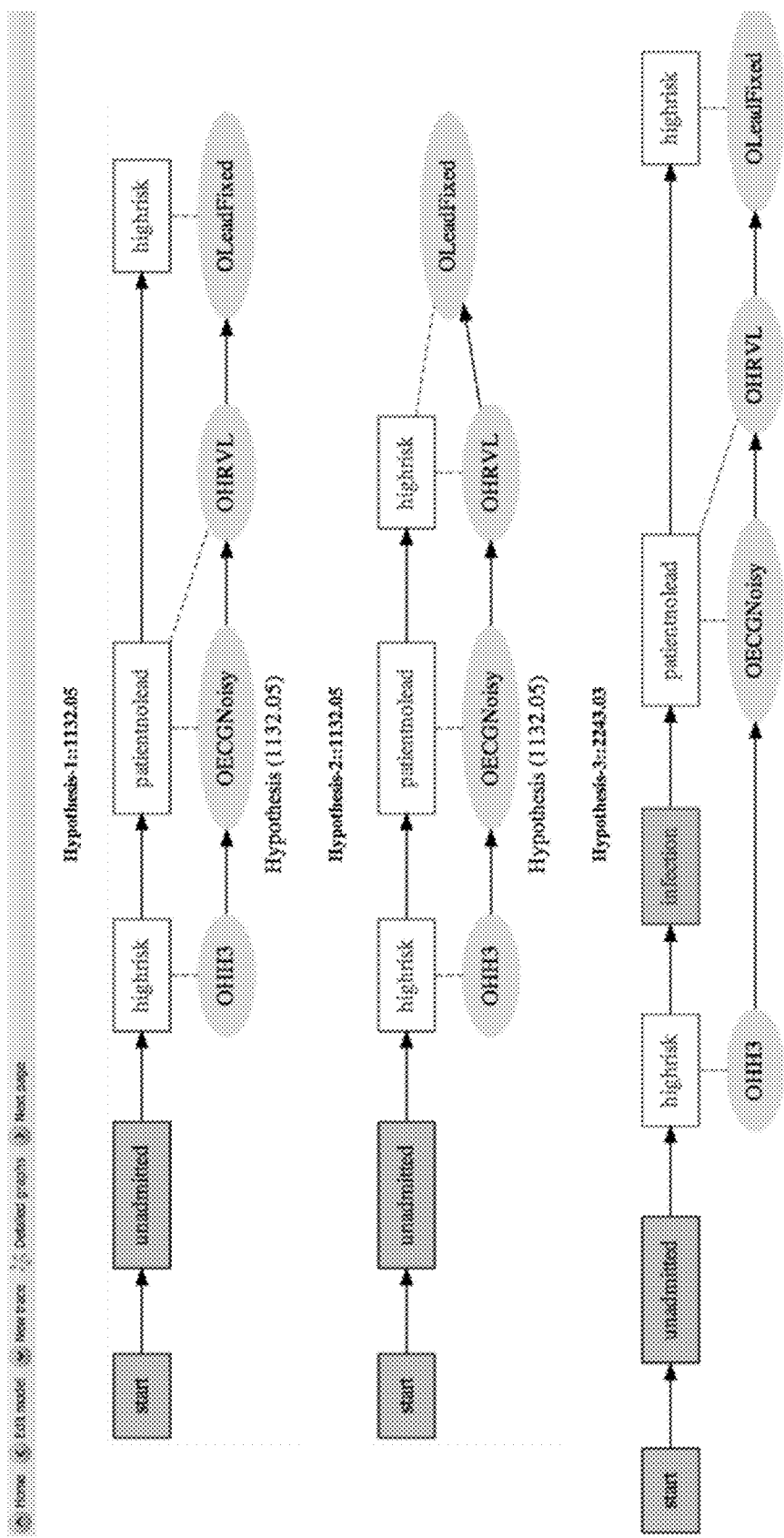

FIGS. 16D and 16E illustrate alternative hypotheses generated for two sample traces in the intensive care delivery application. These are results from more specific less ambiguous observation traces.

Each hypothesis in the model is a sequence of AI planning actions such that each action is defined within the description of the model (a state transition system) and the observation formula is satisfied by the sequence of actions.

EXPERIMENTS

The planning problems in the experiments were described in Planning Domain Definition Language (PDDL). One fixed PDDL planning domain including a total of six planning actions was used in all experiments. Actions explain-observation and discard-observation are used to advance to the next observation in the sequence, and actions state-change and allow-unobserved change the state of the lifecycle. Two additional actions, enter-state-good and enter-state-bad, are used to associate different action costs for good and bad explanations. In at least one implementation, the good states have lower action cost than the bad states: the observed behavior is assumed to not be malicious until it can only be explained as malicious, and the plausibility of hypotheses is computed accordingly. The state transitions of malware lifecycle and the observations are encoded in the problem description. This encoding allowed for automatically generating multiple problem sets that included different number of observations as well as different types of malware lifecycle.

This experimental section is described within the malware detection application.

When the presence of malware is detected inside critical infrastructure, the network administrators have little time to investigate the threat and mitigate it. Thus, malware must be discovered as quickly as possible. However, accuracy is no less important. Critical infrastructure disruptions resulting from overreaction to suspicious-looking observations can be just as undesirable as malware infections themselves.

The described experiments help evaluate the response time and the accuracy of two approaches, LAMA with replanning and MARIO. The lifecycle models need to include descriptions of both non-malicious and malicious behaviors, and may need to be modified regularly to match changes in network configuration and knowledge about malware threats. To study the performance on a wide variety of different lifecycles, a large set of lifecycles were generated randomly. In generating the lifecycles, a directed path was ensured to exist between each pair of states, 60% of the states are bad, 40% are good, and both unique and ambiguous observations can be associated with states. In addition, the performance was evaluated by using a hand-crafted description of the lifecycle illustrated in FIG. 10.

To evaluate performance, the notion of ground truth was introduced. In all of the experiments, the problem instances are generated by constructing a ground truth trace by traversing the lifecycle graph in a random walk. With a probability of 0.5 the ground truth trace contained only good states. For each state, a noisy or missing observation was generated with a probability of 0.025, and ambiguous observations were selected with a probability of 0.25.

Given these observations, each of the generated plans represents a hypothesis about malicious or benign behavior in the network. Then performance was measured by comparing the generated hypotheses with the ground truth, and a problem was considered solved for our purposes if the ground truth appears among the generated hypotheses.

For each size of the problem, ten problem instances were generated, and the measurements presented are averages. The measurements were done on a dual-core 3 GHz Intel Xeon processor and 8 GB memory, running 64-bit RedHat Linux. Each single LAMA invocation was allowed to run up to 20 seconds, except for the first invocation, and all plans produced in that time were saved. Replanning iterations were repeated until a time limit of 300 seconds was reached. A time limit was not set for the first invocation (i.e., the first invocation can take up to 300 seconds). This is because there was a desire for LAMA to find the optimal or near optimal plan (by exhausting the search space) in the first invocation before starting to replan. In the harder problems, if the first invocation did not finish, no replanning was done.

As expected, the method results in many replanning rounds that together help produce many distinct plans. This can be seen in Table 1 showing the average total number of replanning rounds in the Total column, the average number of unfinished rounds that were terminated due to per-round time limit in the Unfinished column, and the average number of distinct plans at the end of iterations in the Plans column. Only distinct plans were counted as independent subtrees in the iterative replanning process may produce duplicates. Also in the smaller size problems, more replanning rounds is done and hence more distinct plans are generated which increases the chance of finding the ground truth.

TABLE 1

| Observations | Hand-crafted | | | 10 states | | | 50 states | | | 100 states | | |
| --- | --- | --- | --- | --- | --- | --- | --- | --- | --- | --- | --- | --- |
| | Plans | Total | Unfinished | Plans | Total | Unfinished | Plans | Total | Unfinished | Plans | Total | Unfinished |
| 5 | 55 | 261 | 0 | 75 | 340 | 0 | 50 | 130 | 0 | 40 | 49 | 0 |
| 10 | 80 | 176 | 0 | 128 | 248 | 0 | 82 | 78 | 0 | 32 | 20 | 1 |
| 20 | 117 | 111 | 0 | 156 | 171 | 0 | 52 | 34 | 0 | 4 | 14 | 13 |
| 40 | 78 | 58 | 0 | 105 | 120 | 0 | 18 | 13 | 11 | 4 | 2 | 2 |
| 60 | 42 | 36 | 0 | 81 | 81 | 0 | 5 | 10 | 9 | 3 | 1 | 1 |
| 80 | 30 | 21 | 4 | 49 | 38 | 0 | 4 | 2 | 2 | 2 | 1 | 1 |
| 100 | 25 | 16 | 8 | 36 | 28 | 3 | 3 | 1 | 1 | 0 | 1 | 1 |
| 120 | 20 | 14 | 12 | 30 | 28 | 5 | 2 | 1 | 1 | 0 | 1 | 1 |

In Tables 1-3, the rows correspond to the number of generated observations and the columns are organized in four groups for different lifecycle types. The handcrafted lifecycle contained 18 lifecycle states and was not changed between the experiments. The generated lifecycles consisted of 10, 50 and 100 states and were re-generated for each experiment, together with the observations.

TABLE 2

| Observations | Hand-crafted | | 10 states | | 50 states | | 100 states | |
| --- | --- | --- | --- | --- | --- | --- | --- | --- |
| | % Solved | Time | % Solved | Time | % Solved | Time | % Solved | Time |
| 5 | 100% | 2.49 | 70% | 0.98 | 80% | 5.61 | 30% | 14.21 |
| 10 | 100% | 2.83 | 90% | 2.04 | 50% | 25.09 | 30% | 52.63 |
| 20 | 90% | 12.31 | 70% | 24.46 | — | — | — | — |
| 40 | 70% | 3.92 | 40% | 81.11 | — | — | — | — |
| 60 | 60% | 6.19 | — | — | — | — | — | — |
| 80 | 50% | 8.19 | — | — | — | — | — | — |

TABLE 2-continued

|  | Hand-crafted | | 10 states | | 50 states | | 100 states | |
| --- | --- | --- | --- | --- | --- | --- | --- | --- |
| Observations | % Solved | Time | % Solved | Time | % Solved | Time | % Solved | Time |
| 100 | 60% | 11.73 | 10% | 10.87 | — | — | — | — |
| 120 | 70% | 20.35 | 20% | 15.66 | — | — | — | — |

TABLE 3

|  | Hand-crafted | | 10 states | | 50 states | | 100 states | |
| --- | --- | --- | --- | --- | --- | --- | --- | --- |
| Observations | % Solved | Time | % Solved | Time | % Solved | Time | % Solved | Time |
| 5 | 100% | 0.16 | 100% | 0.19 | 90% | 0.44 | 80% | 0.92 |
| 10 | 100% | 0.28 | 100% | 0.37 | 90% | 0.76 | 50% | 4.86 |
| 20 | 90% | 1.06 | 90% | 1.18 | 40% | 16.52 | 40% | 6.81 |
| 40 | 80% | 117.57 | 40% | 34.30 | 30% | 73.01 | — | — |
| 60 | 60% | 13.20 | 10% | 301.63 | — | — | — | — |
| 80 | 50% | 5.05 | 10% | 53.45 | — | — | — | — |
| 100 | 50% | 19.82 | — | — | — | — | — | — |
| 120 | 70% | 63.03 | 20% | 161.12 | — | — | — | — |

Tables 2 and 3 summarize the quality of the plans generated in these experiments. Table 2 shows the result of running LAMA, whereas Table 3 shows the result of running MARIO. The % Solved column shows the percentage of problems where the ground truth was among the generated plans. The Time column shows the average time it took from the beginning of iterations (some finished and some unfinished rounds) to find the ground truth solution for the solved problems. The dash entries indicate that the ground truth was not found within the time limit.

The results show that planning can be used successfully to generate hypotheses, even in the presence of unreliable observations, especially for smaller sets of observations or relatively small lifecycles. However, in some of the larger instances LAMA could not find any plans as shown in Table 2. The correct hypothesis was generated in most experiments with up to ten observations. The results for the handcrafted lifecycle also suggest that the problems arising in practice may be easier than randomly generated ones which had more state transitions and a higher branching factor. As shown in Table 3, the results also show that MARIO's performance is better, particularly in the harder instances.

Figure 17:
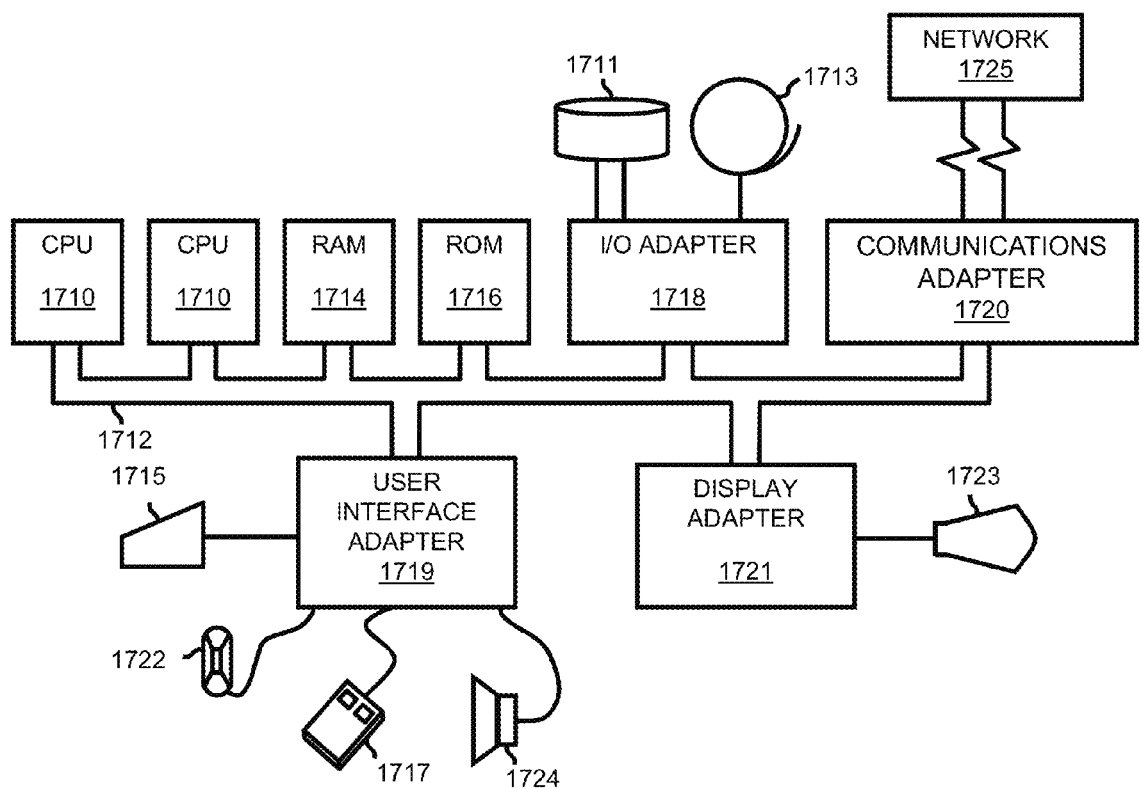
FIG. 17 illustrates a computer program product according to an embodiment of the invention.

Referring now to FIG. 17, a representative hardware environment for practicing at least one embodiment of the invention is illustrated. This schematic drawing illustrates a hardware configuration of an information handling/computer system in accordance with at least one embodiment of the invention. The system comprises at least one processor or central processing unit (CPU) 1710. The CPUs 1710 are interconnected with system bus 1712 to various devices such as a random access memory (RAM) 1714, read-only memory (ROM) 1716, and an input/output (I/O) adapter 1718. The I/O adapter 1718 can connect to peripheral devices, such as disk units 1711 and tape drives 1713, or other program storage devices that are readable by the system. The system can read the inventive instructions on the program storage devices and follow these instructions to execute the methodology of at least one embodiment of the invention. The system further includes a user interface adapter 1719 that connects a keyboard 1715, mouse 1717, speaker 1724, microphone 1722, and/or other user interface devices such as a touch screen device (not shown) to the bus 1712 to gather user input. Additionally, a communication adapter 1720 connects the bus 1712 to a data processing network 1725, and a display adapter 1717 connects the bus 1712 to a display device 1723 which may be embodied as an output device such as a monitor, printer, or transmitter, for example.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A method for operation of a system for predicting hypotheses, the hypotheses comprising explanations of observations, said method comprising:
   receiving a trace from a source of a trace, where a hypotheses generator in the system receives the trace;
   translating the trace and a state transition model into a planning problem, where the hypotheses generator translates the trace and the state transition model into the planning problem;
   producing a set of plans for the trace, where a planner produces the set of plans, each plan including a sequence of action operators, each action operator maps a state into another state;
   translating each plan into a hypothesis, where at least one of the hypotheses generator and the planner translates each plan into the respective hypothesis; and
   returning the hypotheses, where the hypotheses generator returns the hypotheses, and
   wherein at least one of the set of plans includes at least one top-quality plan and the hypotheses includes at least one plausible hypothesis.

2. The method according to claim 1, wherein returning the hypotheses includes
   scoring with the at least one planner each plan based on the cost of the plan associated with the hypothesis; and
   ordering the hypotheses based on the scores of the respective plans.

3. The method according to claim 2, wherein action costs for less probable actions is higher than action costs for more probable actions.

4. The method according to claim 2, wherein actions associated with bad states have a higher action cost than good states.

5. The method according to claim 2, wherein malicious actions have a higher action cost than non-malicious actions.

6. The method according to claim 1, wherein returning the hypotheses includes displaying each hypothesis including any observations present in the trace and the states with linkages between a plurality of the observations and the states,
wherein the hypotheses generator displays the hypotheses on a display, and
wherein each hypothesis is a sequence of actions that explains observations in a system.

7. The method according to claim 1, further comprising at least one of
requesting additional observations; and
alerting an individual of any potential problem determined based on the generated hypotheses where the top hypothesis is indicative of a problem.

8. A method for operation of a system for predicting hypotheses, the hypotheses comprising explanations of observations, said method comprising:
receiving a trace including a request for at least one future observation or at least one past observation from a source of a trace, where a hypotheses generator receives the trace;
translating the trace and a state transition model into a planning problem, where the hypotheses generator translates the trace and the state transition model into the planning problem;
producing a set of plans for the trace, where at least one planner produces the set of plans, each plan including a sequence of action operators, each action operator maps a state into another state;
translating each plan into a hypothesis, where at least one of the hypotheses generator and the at least one planner translates each plan, where at least one hypothesis includes at least one of a future state and a past state; and
returning the hypotheses from the hypotheses generator, and
wherein the set of plans includes at least one top-quality plan and the hypotheses includes at least one plausible hypothesis.

9. The method according to claim 8, wherein the cost of plans is based on the individual costs of the actions present in the plan.

10. The method according to claim 9, wherein the cost of the actions is determined in part based on whether the action is at least one of more plausible or a good action.

11. The method according to claim 8, wherein returning the hypotheses includes displaying each hypothesis by the hypotheses generator through a display including any observations present in the trace and the states with linkages between a plurality of the observations and the states.

12. The method according to claim 8, further comprising returning future observations for at least one hypothesis returned by the hypotheses generator.

13. A system comprising:
at least one planner for the development of a set of plans;
a hypothesis generator in communication with said at least one planner;
a database in communication with said hypothesis generator and said at least one planner;
at least one analytic in communication with said hypotheses generator and said database; and
at least one sensor in communication with one of said at least one analytic, and
wherein at least one of said hypotheses generator and said at least one planner converts each plan in the set of plans into a hypothesis, each plan in the set of plans including a sequence of action operators, each action operator maps a state into another state, the hypothesis comprising an explanation of observations.

14. The system according to claim 13, wherein said at least one analytic converts the data received from said at least one sensor into observations that are at least one of stored in said database and communicated with said hypotheses generator.

15. The system according to claim 14, wherein said hypotheses generator converts the observations and a transition state model into a planning problem that is provided to said at least one planner.

16. The system according to claim 15, wherein said hypotheses generator inserts at least one past observation or at least one future observation into the planning problem.

17. The system according to claim 13, wherein said at least one planner determines a plan cost for each plan based on a predetermined action costs for the actions present in the plan.

18. The system according to claim 17, wherein said hypotheses generator displays each of the resulting hypotheses with a respective score based on the plan cost.

19. A computer program product for predicting hypotheses, the hypotheses comprising explanations of observations, the computer program product comprising:
a non-transitory computer readable storage medium having encoded thereon:
first program instructions executable by a processor to cause the processor to receive a trace;
second program instructions executable by a processor to cause the processor to translate the trace and a state transition model into a planning problem;
third program instructions executable by a processor to cause the processor to produce a set of plans for the trace, each plan including a sequence of action operators, each action operator maps a state into another state;
fourth program instructions executable by a processor to cause the processor to translate each plan into a hypothesis;
fifth program instructions executable by a processor to cause the processor to return the hypotheses; and
wherein at least one of the set of plans include at least one top-quality plan and the hypotheses include at least one most plausible hypothesis.

20. The computer program product according to claim 19, wherein
the trace includes at least one future observation or at least one past observation;
at least one generated hypothesis includes at least one of a future state and one past state.

* * * * *